United States Patent
Liou et al.

(10) Patent No.: US 10,323,122 B2
(45) Date of Patent: Jun. 18, 2019

(54) ELECTROCHROMIC COMPOSITION AND ELECTROCHROMIC ELEMENT

(71) Applicant: INDUSTRIAL TECHNOLOGY RESEARCH INSTITUTE, Hsinchu (TW)

(72) Inventors: Guey-Sheng Liou, Puli Township, Nantou County (TW); Huan-Shen Liu, Taoyuan (TW); De-Cheng Huang, New Taipei (TW); Yu-Ruei Kung, New Taipei (TW); Li-Ting Huang, New Taipei (TW); Chyi-Ming Leu, Jhudong Township, Hsinchu County (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 7 days.

(21) Appl. No.: 15/649,120

(22) Filed: Jul. 13, 2017

(65) Prior Publication Data
US 2018/0186932 A1    Jul. 5, 2018

(30) Foreign Application Priority Data
Dec. 30, 2016   (TW) .............................. 105144138 A

(51) Int. Cl.
*C09K 9/02*   (2006.01)
*G09G 3/38*   (2006.01)
(Continued)

(52) U.S. Cl.
CPC ......... *C08G 69/265* (2013.01); *C08G 73/026* (2013.01); *C08G 73/028* (2013.01);
(Continued)

(58) Field of Classification Search
CPC ........ C08G 63/00; C08G 63/02; C08G 63/12; C08G 63/16; C08G 69/26; C08G 69/265;
(Continued)

(56) References Cited

U.S. PATENT DOCUMENTS 7,214,762 B1 *  5/2007  Mitani ............... C08G 18/3859
                                                      429/213
7,879,492 B2 *  2/2011  Armand ................ H01M 4/137
                                                      429/213
(Continued)

FOREIGN PATENT DOCUMENTS

CN    103834009 A    6/2014
CN    105175716 A    12/2015
(Continued)

OTHER PUBLICATIONS

Beaujuge, P.M. et al. "The donor-acceptor approach allows a black-to-transmissive switching polymeric electrochrome" Nature Materials, 7, Oct. 2008, pp. 795-799.
(Continued)

*Primary Examiner* — Loha Ben
(74) *Attorney, Agent, or Firm* — Birch, Stewart, Kolasch & Birch, LLP

(57) ABSTRACT

An electrochromic composition is provided. The electrochromic composition includes 0.5~10 parts by weight of a first oxidizable polymer, 0.5~10 parts by weight of a reducible organic compound, 0.5~20 parts by weight of an electrolyte, and 60~98.5 parts by weight of a solvent. The first oxidizable polymer is a polymer of 1 molar part of diamine and 0.1~20 molar parts of dicarboxylic acid, diacyl chloride, or dianhydride, a mixture of the aforementioned polymers, or a copolymer of the aforementioned polymers. An electrochromic element including the aforementioned electrochromic composition is also provided.

21 Claims, 8 Drawing Sheets

(51) Int. Cl.
| | |
|---|---|
| *C08G 69/26* | (2006.01) |
| *C08G 73/02* | (2006.01) |
| *C08G 73/10* | (2006.01) |
| *G01N 21/31* | (2006.01) |
| *G02F 1/361* | (2006.01) |
| *C09D 179/08* | (2006.01) |
| *G02F 1/1516* | (2019.01) |
| *F21V 9/00* | (2018.01) |
| *C08K 5/092* | (2006.01) |

(52) U.S. Cl.
CPC ..... *C08G 73/0273* (2013.01); *C08G 73/1042* (2013.01); *C08G 73/1078* (2013.01); *C09D 179/08* (2013.01); *C09K 9/02* (2013.01); *G02F 1/3615* (2013.01); *G09G 3/38* (2013.01); *C08K 5/092* (2013.01); *F21V 9/00* (2013.01); *G01N 21/31* (2013.01); *G02F 1/15165* (2019.01)

(58) Field of Classification Search
CPC ........ C08G 69/42; C08G 69/48; C08G 73/02; C08G 73/024; C08G 73/026; C08G 73/0266; C08G 73/06; C08G 75/205; C08G 75/22; C08G 73/1078; C08G 73/0273; C08G 73/028; C08G 73/1042; C09K 9/00; C09K 9/02; C09K 2211/1059; C09K 2211/1466; G01N 21/31; G02F 1/0018; G02F 1/15; G02F 1/1508; G02F 1/1525; G02F 1/153; G02F 1/361; G02F 1/3615; G02F 2001/1515; G02F 1/15165; F21V 9/00; H01B 1/12; G09G 3/38; C08K 5/09; C08K 5/092; C08K 5/45; C09D 179/08
USPC ................ 359/265, 270, 274, 275; 345/105; 252/500, 510, 582, 583, 589; 257/40; 430/7, 18, 191–193; 528/98, 373, 390
See application file for complete search history.

(56) References Cited

U.S. PATENT DOCUMENTS

| | | |
|---|---|---|
| 7,894,118 B2 | 2/2011 | Hirano et al. |
| 8,014,056 B2 | 9/2011 | Kokeguchi et al. |
| 8,343,381 B1 * | 1/2013 | Chesterfield ........... C08G 61/12 252/500 |
| 8,404,800 B2 | 3/2013 | Beaujuge et al. |
| 8,435,696 B2 * | 5/2013 | Palmore .............. H01M 4/8807 429/482 |
| 9,164,345 B2 | 10/2015 | Konkin et al. |
| 9,184,390 B2 * | 11/2015 | You ..................... H01L 51/0036 |
| 9,209,403 B2 * | 12/2015 | Tseng ................. C08G 73/1039 |
| 9,331,280 B2 * | 5/2016 | Kung ................. H01L 51/0035 |
| 9,589,538 B2 * | 3/2017 | Davidson ................ G09G 5/32 |

FOREIGN PATENT DOCUMENTS

| | | |
|---|---|---|
| CN | 105503775 A | 4/2016 |
| TW | I468440 B | 1/2015 |
| TW | I486430 B | 6/2015 |
| TW | 201533228 A | 9/2015 |

OTHER PUBLICATIONS

Hsiao, Sheng-Huei et al. "Novel Aromatic Polyamides and Polyimides Functionalized with 4-tert-Butyltriphenylamine Groups" Journal of Polymer Science: Part A: Polymer Chemistry, 44, 2006, pp. 4579-4592.

Shi, Pengjie et al. "Broadly Absorbing Black to Transmissive Switching Electrochromic Polymers" Advanced Materials, 2010, 22, pp. 4949-4953.

Weng, Duo et al. "High performance black-totransmissive electrochromic device with panchromatic absorption based on TiO2-supported viologen and triphenylamine derivatives" Organic Electronics, 34, 2016, pp. 139-145.

Xu, Zhangping et al. "Black-to-transmissive electrochromic switching polymer films via solution co-processing" New Journal of Chemistry, 2016, 40, pp. 5231-5237.

Yen, Hung-Ju et al. "Solution-Processable Novel Near-Infrared Electrochromic Aromatic Polyamides Based on Electroactive Tetraphenyl-p-Phenylenediamine Moieties" American Chemical Society, 2009, 21, pp. 4062-4070.

Yen, Hung-Ju et al. "Transmissive to black electrochromic aramids with high near-infrared and multicolor electrochromism based on electroactive tetraphenylbenzidine unites" Journal of Materials Chemistry, 2011, 21, pp. 6230-6237.

Taiwanese Office Action for Appl. No. 105144138 dated Oct. 27, 2017.

* cited by examiner

ELECTROCHROMIC COMPOSITION AND ELECTROCHROMIC ELEMENT

CROSS REFERENCE TO RELATED APPLICATIONS

This application is based on, and claims priority from, Taiwan Application Number 105144138, filed on Dec. 30, 2016, the disclosure of which is hereby incorporated by reference herein in its entirety.

BACKGROUND

Field of the Invention

The present invention relates to an electrochromic composition and an electrochromic element.

Description of the Related Art

Electrochromic-related devices are attractive in green energy industries due to their low driving voltage (<3.0V) and bistability. The technique is deemed as an important industry in future decades, and electrochromic materials play an important role in the industry. Recently, the major part of electrochromic material is inorganic oxides for longer lifetime and endurance; however, films thereof are prepared by using expensive processes and equipment such as vacuum deposition, spray pyrolysis, or sputtering. Even ignoring the cost of processing, an inorganic oxide still has shortcomings such as a slow electrochromic rate, less color variation, and the like. In an organic system, electrochromic materials use conjugated polymer with more color variations and fast electrochromic rates. However, the conjugated compound has shortcomings such as expensive monomers, complicated synthesis, and formation by electro-polymerization. The electrochromic conjugated polymer has a deep color due to its conjugated length. Although the deep color can be lightened by applying a voltage, the conjugated polymer cannot be fully transparent. In other words, the conjugated polymer must be electrified to achieve a transparent state, thereby leading to the problem of high energy consumption.

Small molecules such as triarylamine and its derivatives have good electron hole conductive properties, and are mostly applied to the electron conductive layer of an organic light-emitting diode (OLED), and may also be applied in electrochromic applications. However, so far, the derivatives of triarylamine cannot appear as truly black in electrochromic applications.

To sum up the information above, a novel electrochromic organic material is currently needed to simultaneously achieve the goals of possessing high transparent property at usual time and possessing a high shielding effect after an electrochromic reaction.

BRIEF SUMMARY OF THE INVENTION

According to an embodiment, an electrochromic composition is provided. The electrochromic composition includes 0.5~10 parts by weight of a first oxidizable polymer, 0.5~10 parts by weight of a reducible organic compound, 0.5~20 parts by weight of an electrolyte, and 60~98.5 parts by weight of a solvent. The first oxidizable polymer is a polymer of 1 molar part of diamine and 0.1~20 molar parts of dicarboxylic acid, diacyl chloride, or dianhydride, a mixture of the aforementioned polymers, or a copolymer of the aforementioned polymers. The diamine is Formula 1, Formula 2, or a combination thereof:

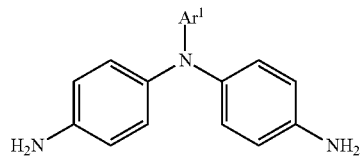
(Formula 1)

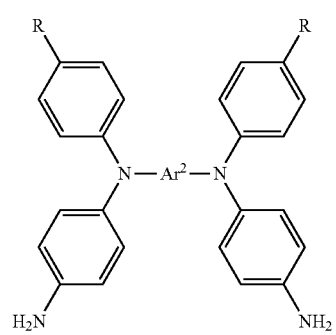
(Formula 2)

$Ar^1$ is Formula 3, Formula 4, Formula 5, Formula 6, Formula 7, or Formula 8:

(Formula 3)

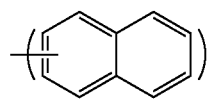
(Formula 4)

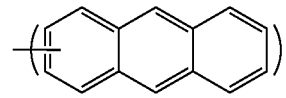
(Formula 5)

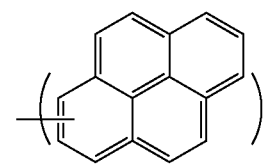
(Formula 6)

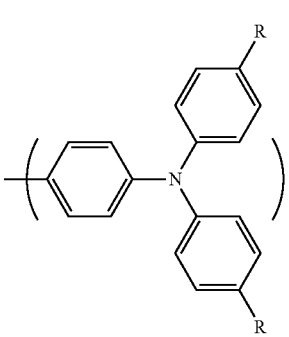
(Formula 7)

-continued (Formula 8)

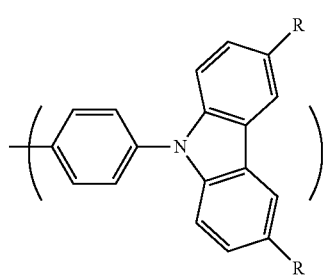

R is —H, —F, —Br, —Cl, —I, —CH$_3$, —C$_2$H$_5$, —C$_3$H$_7$, -n-C$_4$H$_9$, -s-C$_4$H$_9$, -t-C$_4$H$_9$, —C$_5$H$_{11}$, —C$_6$H$_{13}$, —C$_7$H$_{15}$, —OCH$_3$, —OC$_2$H$_5$, —OC$_3$H$_7$, -n-OC$_4$H$_9$, -s-C$_4$H$_9$, -t-C$_4$H$_9$, —OC$_5$H$_{11}$, —OC$_6$H$_{13}$, or —OC$_7$H$_{15}$;

Ar$^2$ is Formula 9, Formula 10, Formula 11, or Formula 12:

(Formula 9)

(Formula 10)

(Formula 11)

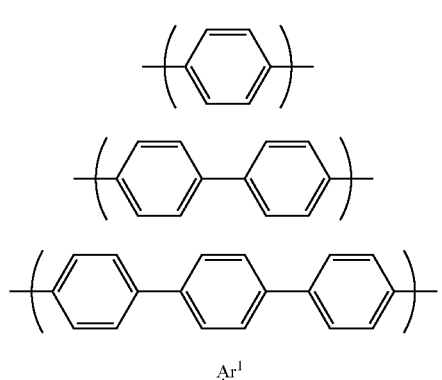

(Formula 12)

wherein the dicarboxylic acid is Formula 13, the diacyl chloride is Formula 14, and the dianhydride is Formula 15:

(Formula 13)

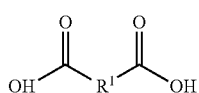

(Formula 14)

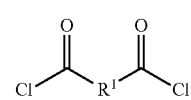

(Formula 15)

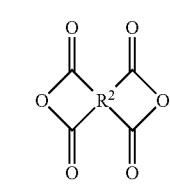

R$^1$ is selected from the group consisting of —(CH$_2$)$_n$—, Formula 9, Formula 16, Formula 17, Formula 18, Formula 19, Formula 20, Formula 21, Formula 22, Formula 23, and Formula 24, wherein n is between 1 and 12:

(Formula 9)

(Formula 16)

(Formula 17)

(Formula 18)

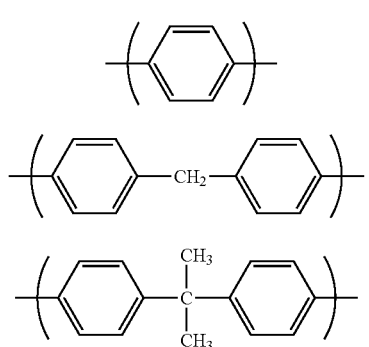

(Formula 19)

(Formula 20)

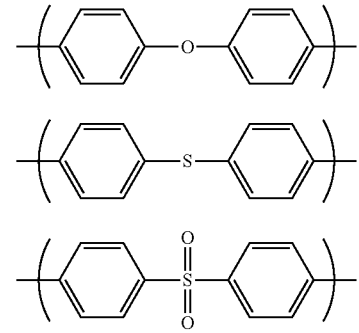

(Formula 21)

(Formula 22)

(Formula 23)

(Formula 24)

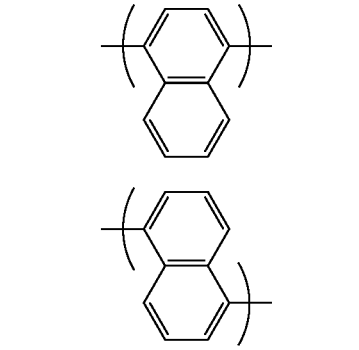

R$^2$ is cyclic aliphatic or organic aromatic.

According to another embodiment, an electrochromic element is provided. The electrochromic element includes a first transparent conductive layer, a second transparent conductive layer disposed opposite to the first transparent conductive layer, an adhesive spacer, connected to the surfaces of the first transparent conductive layer and the second transparent conductive layer. The first transparent conductive layer, the second transparent conductive layer, and the adhesive spacer form a cell. Then, the aforementioned electrochromic composition is filled in the cell.

According to still another embodiment, an electrochromic element is provided. The electrochromic element includes a first transparent conductive layer, a second transparent conductive layer disposed opposite to the first transparent conductive layer, a film layer disposed on the first transparent conductive layer and composed of the aforementioned first oxidizable polymer, and an adhesive spacer, connected to the surfaces of the film layer and the second transparent conductive layer. The film layer, the second transparent conductive layer, and the adhesive spacer form a cell. Then, an electrolyte layer is filled in the cell. The electrolyte layer is composed of the aforementioned reducible organic compound, electrolyte, and solvent.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

Figure 1A:
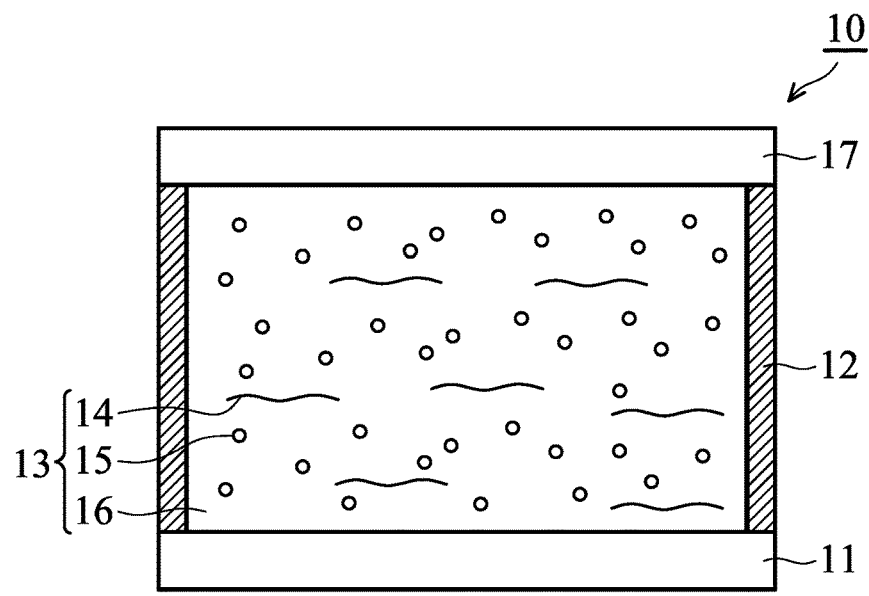
FIG. 1A illustrates a schematic diagram of an electrochromic element in accordance with an embodiment of the present disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The present invention will be described with respect to particular embodiments and with reference to certain drawings, but the invention is not limited thereto and is only limited by the claims. The drawings described are only schematic and are non-limiting. In the drawings, the size of some of the elements may be exaggerated for illustrative purposes and are not drawn to scale. The dimensions and the relative dimensions do not correspond to actual dimensions in the practice of the invention.

The present disclosure provides an electrochromic composition by using a bipolar design of an oxidizable organic polymer and a reducible organic small molecule. The neutral state of the electrochromic composition has a high transparency and can decrease the driving voltage and improve the electrochemical stability. In addition, the transmittance of the redox state of electrochromic composition may be reduced by the complementation of the colors produced by the oxidizable organic polymer and the reducible organic small molecule, making the electrochromic composition have a deeper color, or even truly black.

The first oxidizable polymer is a polymer of a molar part of diamine and 0.1~20 molar parts of dicarboxylic acid, diacyl chloride, or dianhydride, a mixture of the aforementioned polymers, or a copolymer of the aforementioned polymers. An overly high ratio of dicarboxylic acid, diacyl chloride, or dianhydride may lower the color change contrast of the electrochromic composition in an oxidation state. An overly low ratio of dicarboxylic acid, diacyl chloride, or dianhydride may increase the electrochromic oxidation active sites, and coupling side reactions can easily occur. The diamine is Formula 1, Formula 2, or a combination thereof:

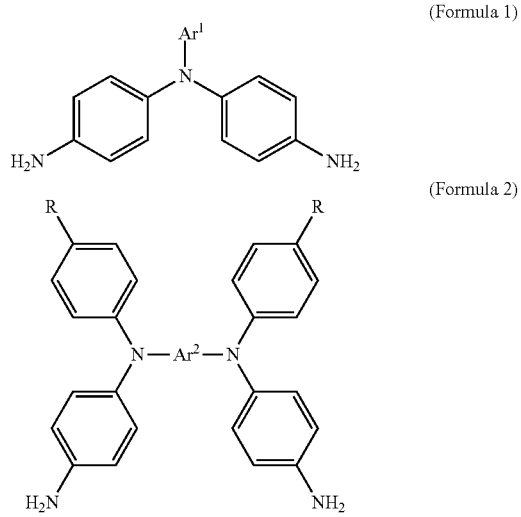

In Formula 1, $Ar^1$ is Formula 3, Formula 4, Formula 5, Formula 6, Formula 7, or Formula 8:

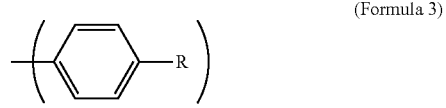

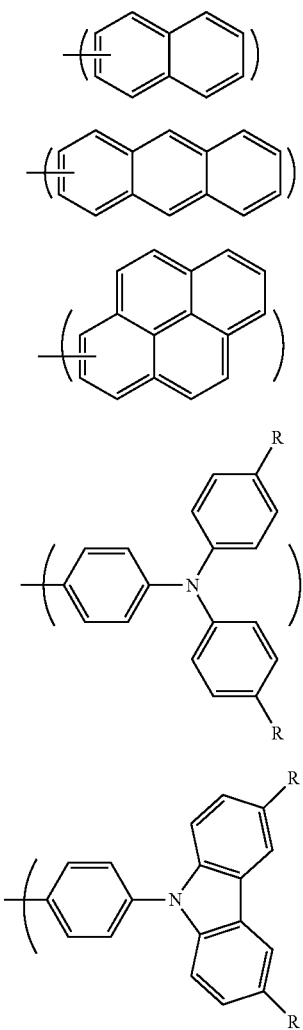
(Formula 4)

(Formula 5)

(Formula 6)

(Formula 7)

(Formula 8)

In Formula 3, Formula 7, and Formula 8, R is —H, —F, —Br, —Cl, —I, —CH$_3$, —C$_2$H$_5$, —C$_3$H$_7$, -n-C$_4$H$_9$, -s-C$_4$H$_9$, -t-C$_4$H$_9$, —C$_5$H$_{11}$, —C$_6$H$_{13}$, —C$_7$H$_{15}$, —OCH$_3$, —OC$_2$H$_5$, —OC$_3$H$_7$, -n-OC$_4$H$_9$, -s-OC$_4$H$_9$, -t-OC$_4$H$_9$, —OC$_5$H$_{11}$, —OC$_6$H$_{13}$, or —OC$_7$H$_{15}$.

In Formula 2, Ar$^2$ is Formula 9, Formula 10, Formula 11, or Formula 12. In Formula 12, the definition of Ar$^1$ is the same as described above, and hence is not described again to avoid unnecessary repetition.

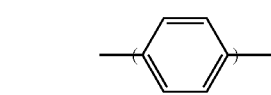
(Formula 9)

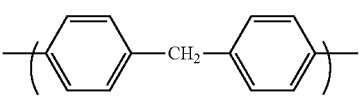
(Formula 10)

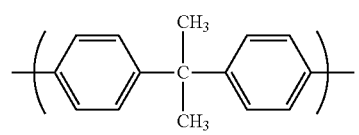
(Formula 11)

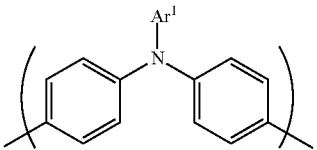
(Formula 12)

The aforementioned dicarboxylic acid is Formula 13, the aforementioned diacyl chloride is Formula 14, and the aforementioned dianhydride is Formula 15:

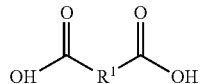
(Formula 13)

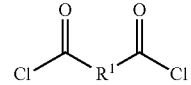
(Formula 14)

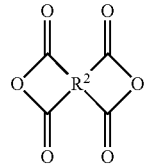
(Formula 15)

In Formula 13 and Formula 14, R$^1$ is selected from the group consisting of —(CH$_2$)$_n$—, Formula 9, Formula 16, Formula 17, Formula 18, Formula 19, Formula 20, Formula 21, Formula 22, Formula 23, and Formula 24, wherein n is between 1 and 12. If the number n is too large, the heat resistance of the electrochromic material decreases. If the number n is too small, the solubility of the electrochromic material decreases.

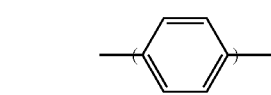
(Formula 9)

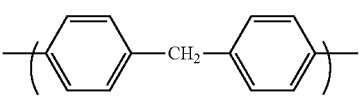
(Formula 16)

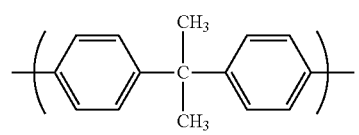
(Formula 17)

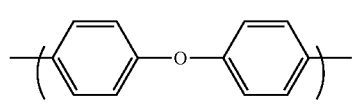
(Formula 18)

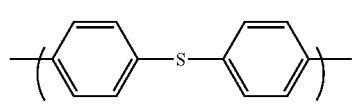
(Formula 19)

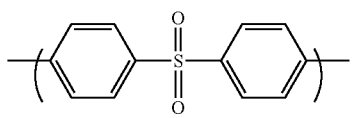
(Formula 20)

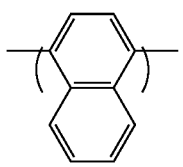
(Formula 21)

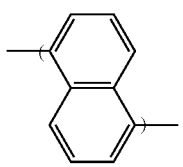
(Formula 21)

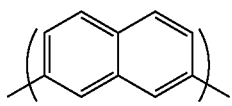
(Formula 23)

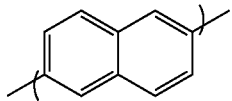
(Formula 24)

In Formula 15, $R^2$ is cyclic aliphatic or organic aromatic.

In an embodiment of the present disclosure, the intermediate products of dinitro may be manufactured in accordance with the synthetic methods described in J. Polym. Sci. Part A: Polym. Chem. 2006, 44, pp4579-4592 and J. Mater. Chem. 2011, 21, 6230-6237. Then, the diamine monomers, for example, monomers such as triphenylamine diamine, triarylamine diamine, pentaphenyl diamine, hexaphenyldiamine derived from triphenylamine (TPA), N,N,N',N'-tetraphenyl-p-phenylenediamine (TPPA), N, N,N',N'-tetraphenylbenzidine (TPB), may be obtained from the intermediate products of dinitro through a reduction reaction. Then, the dicarboxylic acid, diacid chloride, or dianhydride of various aromatics and aliphatics undergo a condensation reaction with diamine monomers to obtain transparent oxidizable organic polymers. The aforementioned transparent oxidizable organic polymers may be applied not only to the electrochromic elements, but they may also be applicable as compounds with electron conductive properties used in the redox sensors, semiconductors, solar batteries, organic electroluminescent devices, nonlinear materials, etc.

The transparent oxidizable organic polymers produced by the condensation reaction of the aforementioned diamine, and the dicarboxylic acid, diacid chloride, or dianhydride of various aromatics and aliphatics may include polymers having a structure represented by Formula 25, Formula 26, Formula 27, or Formula 28, or a copolymer of the aforementioned polymers:

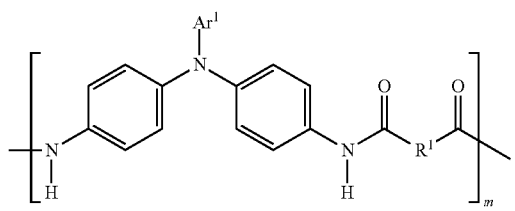
(Formula 25)

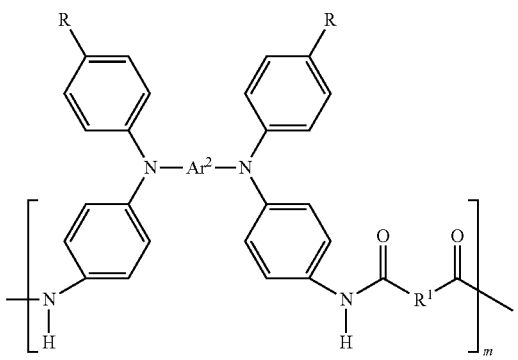
(Formula 26)

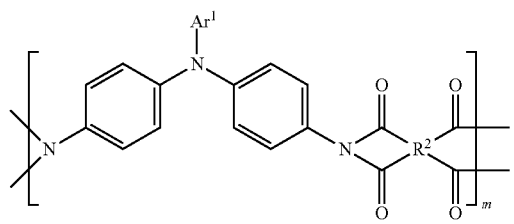
(Formula 27)

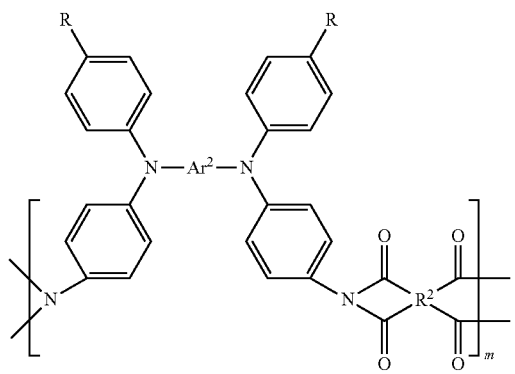
(Formula 28)

In Formula 25, Formula 26, Formula 27, Formula 28, the definition of $Ar^1$, $Ar^2$, R, $R^1$, $R^2$ is the same as described above, wherein m is between 1 and 300. If m is too large, the viscosity is too large and it is inconvenient for the coating process. If m is too small, the molecular weight is not high enough which results in poor film-forming properties, causing poor heat resistance and lowering the range of applicable operative temperatures.

In an embodiment of the present disclosure, the aforementioned transparent oxidizable organic polymers may include a copolymer of the polymer having a structure represented by Formula 25, as shown by Formula 29:

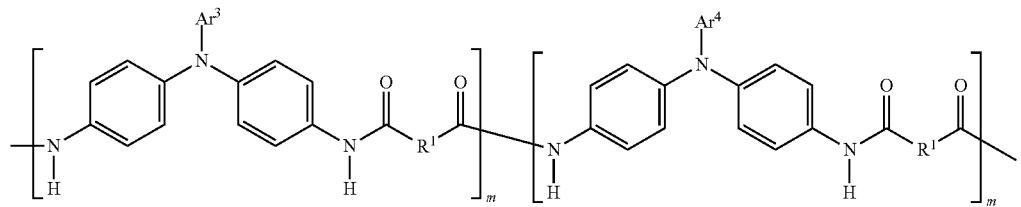

(Formula 29)

In Formula 29, each of $Ar^3$ and $Ar^4$ may independently be Formula 3, Formula 4, Formula 5, Formula 6, Formula 7, or Formula 8, wherein $Ar^3$ and $Ar^4$ are different, and m is between 1 and 300. When forming the copolymer shown by Formula 29, the molar ratio of the polymer monomer including $Ar^3$ functional group to the polymer monomer including $Ar^4$ functional group may be between 99:1 and 1:99.

In an embodiment of the present disclosure, the aforementioned transparent oxidizable organic polymers may include a copolymer of polymers having a structure represented by Formula 26, as shown by Formula 30:

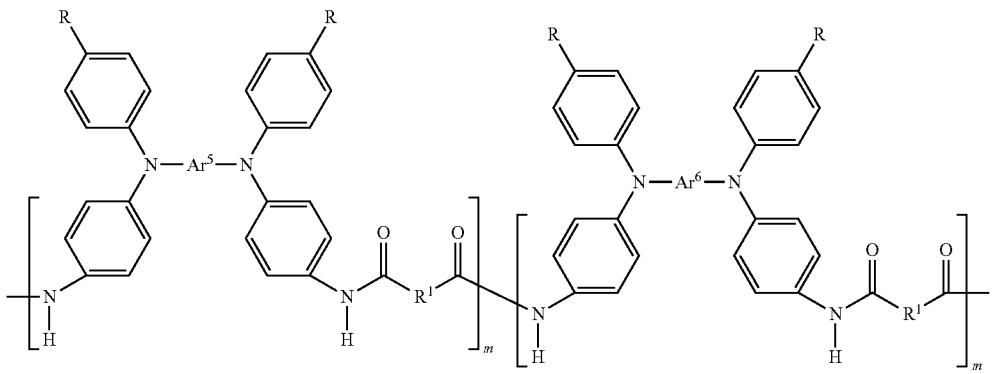

(Formula 30)

In Formula 30, each of $Ar^5$ and $Ar^6$ may independently be Formula 9, Formula 10, Formula 11, or Formula 12, wherein $Ar^5$ and $Ar^6$ are different, and m is between 1 and 300. When forming the copolymer shown by Formula 30, the molar ratio of the polymer monomer including $Ar^5$ functional group to the polymer monomer including $Ar^6$ functional group may be between 99:1 and 1:99.

In an embodiment of the present disclosure, the aforementioned transparent oxidizable organic polymers may include a copolymer of polymers having a structure represented by Formula 27, as shown by Formula 31:

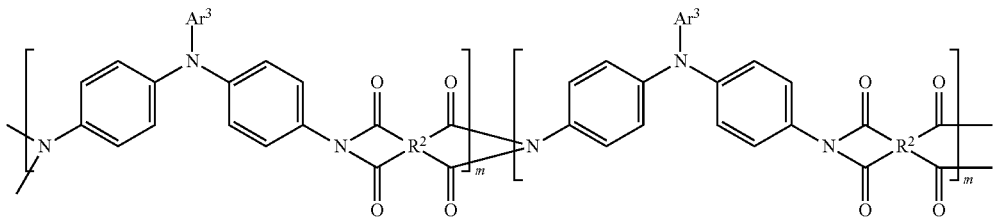

(Formula 31)

In Formula 31, each of $Ar^3$ and $Ar^4$ may independently be Formula 3, Formula 4, Formula 5, Formula 6, Formula 7, or Formula 8, wherein $Ar^3$ and $Ar^4$ are different, and m is between 1 and 300. When forming the copolymer shown by Formula 31, the molar ratio of the polymer monomer including $Ar^3$ functional group to the polymer monomer including $Ar^4$ functional group may be between 99:1 and 1:99.

In an embodiment of the present disclosure, the aforementioned transparent oxidizable organic polymers may include a copolymer of polymers having a structure represented by Formula 28, as shown by Formula 32:

organic polymer formed through the polymerization thereof is represented by Formula 25, wherein $Ar^1$ has a structure represented by Formula 3, R is —$OCH_3$, and $R^1$ is —$(CH_2)_4$—.

(Formula 32)

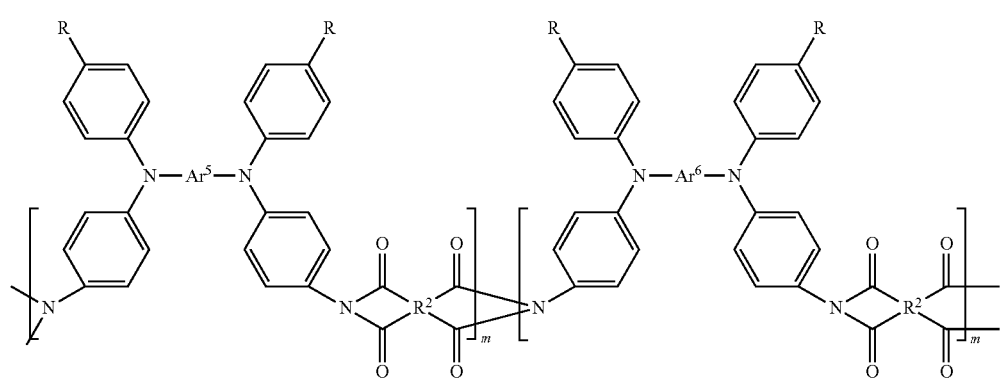

In Formula 32, each of $Ar^5$ and $Ar^6$ may independently be Formula 9, Formula 10, Formula 11, or Formula 12, wherein $Ar^5$ and $Ar^6$ are different, and m is between 1 and 300. When forming the copolymer shown by Formula 32, the molar ratio of the polymer monomer including $Ar^5$ functional group to the polymer monomer including $Ar^6$ functional group may be between 99:1 and 1:99.

In an embodiment of the present disclosure, the aforementioned diamine is Formula 33, the aforementioned dicarboxylic acid is Formula 34, and the transparent oxidizable organic polymer formed through the polymerization thereof is represented by Formula 25, wherein $Ar^1$ has a structure represented by Formula 3, R is —$OCH_3$, and $R^1$ has a structure represented by Formula 18.

(Formula 33)

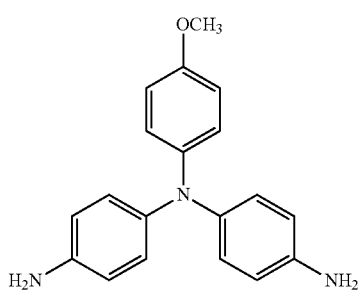

(Formula 35)

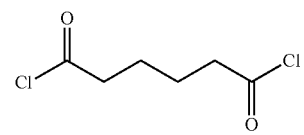

In an embodiment of the present disclosure, the aforementioned diamine is Formula 36, the aforementioned dicarboxylic acid is Formula 34, and the transparent oxidizable organic polymer formed through the polymerization thereof is represented by Formula 26, wherein $Ar^2$ has a structure represented by Formula 9, R is —$OCH_3$, and $R^1$ has a structure represented by Formula 18.

(Formula 33)

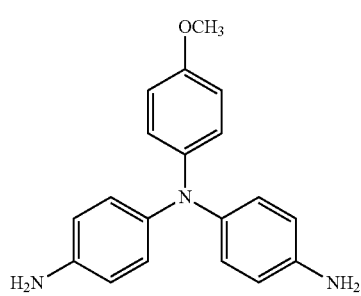

(Formula 34)

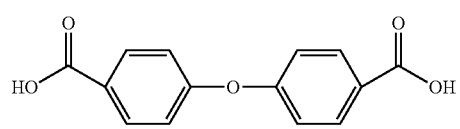

In an embodiment of the present disclosure, the aforementioned diamine is Formula 33, the aforementioned diacyl chloride is Formula 35, and the transparent oxidizable (Formula 36)

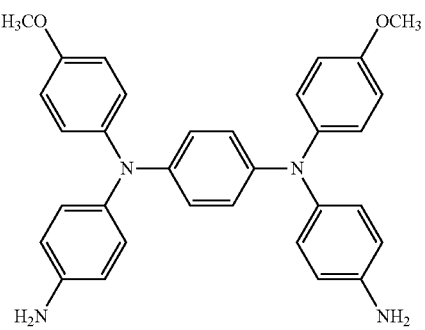

(Formula 34)

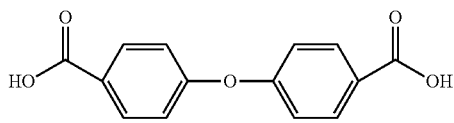

In an embodiment of the present disclosure, the aforementioned diamine is Formula 36, the aforementioned diacyl chloride is Formula 35, and the transparent oxidizable organic polymer formed through the polymerization thereof is represented by Formula 26, wherein $Ar^2$ has a structure represented by Formula 9, R is —$OCH_3$, and $R^1$ is —$(CH_2)_4$—.

(Formula 36)

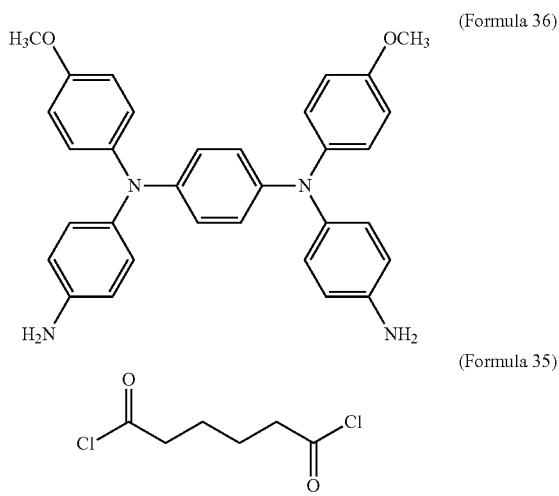

(Formula 35)

In an embodiment of the present disclosure, the aforementioned diamine is Formula 37, the aforementioned dicarboxylic acid is Formula 34, and the transparent oxidizable organic polymer formed through the polymerization thereof is represented by Formula 26, wherein $Ar^2$ has a structure represented by Formula 10, R is —$OCH_3$, and $R^1$ has a structure represented by Formula 18.

(Formula 37)

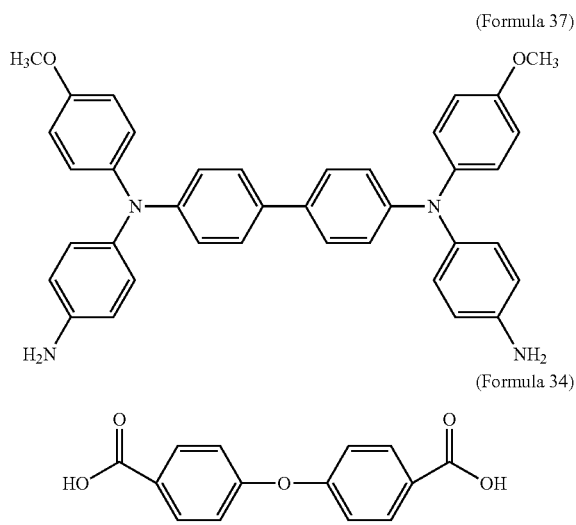

(Formula 34)

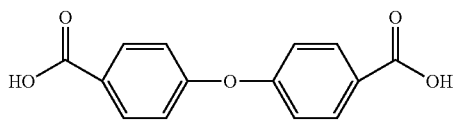

In an embodiment of the present disclosure, the aforementioned diamine is Formula 37, the aforementioned diacyl chloride is Formula 35, and the transparent oxidizable organic polymer formed through the polymerization thereof is represented by Formula 26, wherein $Ar^2$ has a structure represented by Formula 10, R is —$OCH_3$, and $R^1$ is —$(CH_2)_4$—.

(Formula 37)

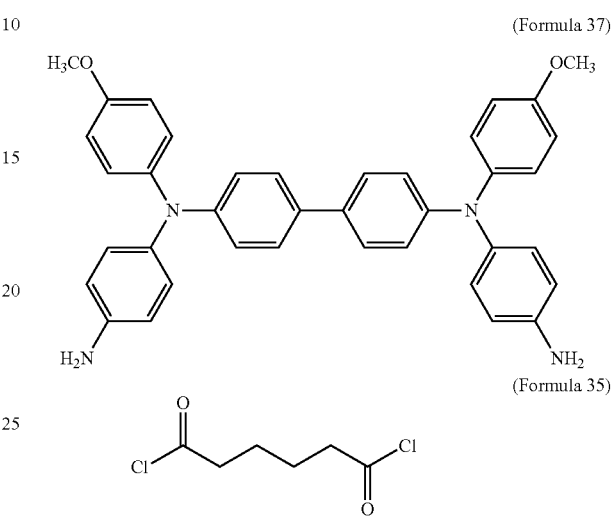

(Formula 35)

In an embodiment of the present disclosure, the aforementioned reducible organic compound is Formula 38, Formula 39, Formula 40, derivatives thereof, or a combination thereof:

(Formula 38)

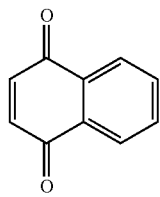

(Formula 39)

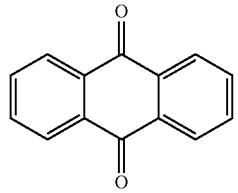

(Formula 40)

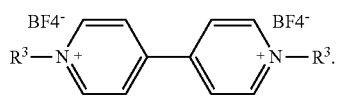

In Formula 40, $R^3$ is H or $C_1$–$C_{12}$ alkyl. In an embodiment of the present disclosure, $R^3$ is $C_7H_{15}$.

In an embodiment of the present disclosure, the aforementioned electrolyte may be organic ammonium salts or inorganic ammonium salts. In one embodiment of the present disclosure, the electrolyte may contain at least one inert conducting salt. Examples of suitable inert conducting salts include lithium salts, sodium salts, and tetraalkylammonium salts. Suitable solvents include solvents which are redox-inert at the selected voltages and which cannot dissociate to form electrophiles or nucleophiles, or the solvents themselves cannot react as sufficiently strong electrophiles or nucleophiles, and thus could not react with the colored ionic free radicals. Examples of suitable solvents include propylene carbonate (PC), gamma-butyrolactone (GBL, γ-butyrolactone), acetonitrile, propionitrile, glutaronitrile, methylglutaronitrile, 3,3'-oxydipropionitrile, hydroxypropionitrile, dimethylformamide, N-methylpyrrolidone, sulfolane, 3-methylsulfolane, or mixtures thereof. Preferable solvents are propylene carbonate (PC) and the mixture of propylene carbonate (PC) and glutaronitrile. The concentration of the electrolyte may be between 0.01 M and 3.0 M.

In an embodiment of the present disclosure, the molar ratio of the aforementioned transparent oxidizable polymer to the reducible organic polymer may be between about 1:50 and 50:1. By controlling the ratio of the transparent oxidizable polymer to the reducible organic polymer, an effect of changing colors may be accomplished. In one embodiment, the molar ratio of the transparent oxidizable polymer to the electrolyte may be between 1:1 and 1:300. In one embodiment, the molar ratio of the reducible organic compound to the electrolyte may be between 1:1 and 1:300. An overly low ratio of the electrolyte may slow down the rate of color-changing and color-fading.

In an embodiment of the present disclosure, the weight average molecular weight of the transparent oxidizable polymer may be between 1,000 and 300,000. If the weight average molecular weight of the transparent oxidizable polymer is too high, the viscosity is too high and it is inconvenient for the coating process. If the weight average molecular weight of the transparent oxidizable polymer is too low, the film-forming properties of the polymer are poor.

In an embodiment of the present disclosure, the transparent oxidizable polymer may be a film layer, and the thickness of the film layer may be between 50 nm and 50 µm. If the thickness of the film layer is too thin, the contrast of the full band is lower. If the thickness of the film layer is too thick, it is difficult to appear as truly black after the electrochromic reaction through the interaction with the electrolytes.

The electrochromic composition is obtained after mixing 0.5~10 parts by weight of the transparent oxidizable polymers and 0.5~10 parts by weight of the reducible organic compounds with the electrolyte solution (including 0.5~20 parts by weight of the electrolyte and 60~98.5 parts by weight of the solvent). In an embodiment of the present disclosure, the transparent oxidizable polymer may be a film layer, which may form the electrochromic composition of the present disclosure with an electrolyte layer combination including the reducible organic compounds, the electrolyte, and the solvent.

In one embodiment, as shown in FIG. 1A, the electrochromic element 10 provided by the present disclosure includes a first transparent conductive layer 11, and a second transparent conductive layer 17 disposed opposite to the first transparent conductive layer 11. An adhesive spacer 12 is connected to the surfaces of the first transparent conductive layer 11 and the second transparent conductive layer 17, and forms a cell with the first transparent conductive layer 11 and the second transparent conductive layer 17. The electrochromic composition 13 is filled in the cell. The electrochromic composition 13 may be formed by mixing an oxidizable polymer 14 and a reducible organic compound 15, and then adding an electrolyte solution 16 including electrolyte and solvent. In other embodiments, the electrochromic composition 13 may further include a second oxidizable organic compound (not shown) other than the oxidizable polymer 14 and the reducible organic compound 15.

Figure 1B:
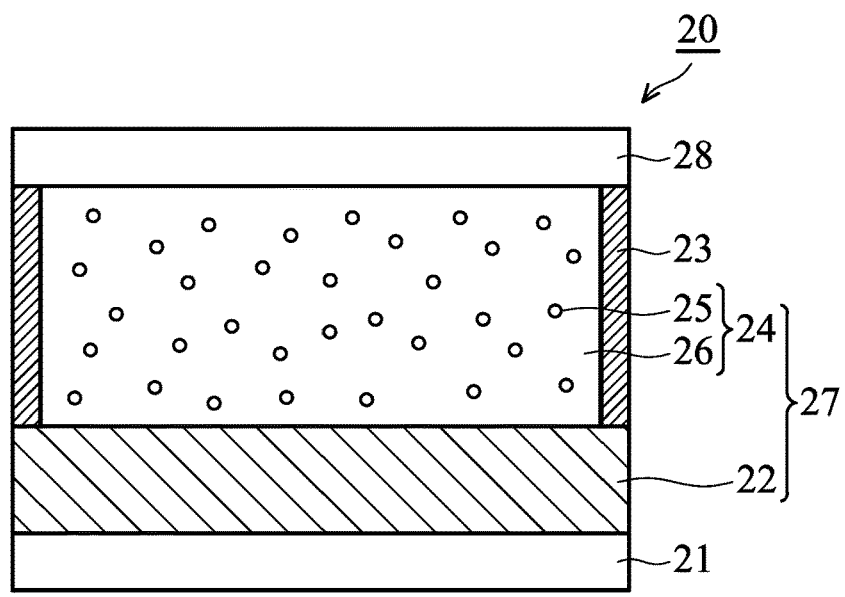
FIG. 1B illustrates a schematic diagram of an electrochromic element in accordance with another embodiment of the present disclosure.

In another embodiment, as shown in FIG. 1B, the electrochromic element 20 provided by the present disclosure includes a first transparent conductive layer 21, and a second transparent conductive layer 28 disposed opposite to the first transparent conductive layer 21. The oxidizable polymer solution may be coated on the first transparent conductive layer 21 using a wet coating method. A film layer 22 is formed after baking. The adhesive spacer 23 connects with the surface of the film layer 22 and the surface of the second transparent conductive layer 28 facing the surface of the film layer 22. A cell is formed by the adhesive spacer 23, the film layer 22, and the second transparent conductive layer 28. The electrolyte is dissolved in a solvent to form an electrolyte solution 26. The electrolyte solution 26 which includes reducible organic compound 25 is used as an electrolyte layer 24 to fill the cell. In another embodiment, the electrolyte layer 24 is in a gel state, and may be coated on the film layer 22 using the same wet coating method. Then, the second transparent conductive layer 28 is attached. In this embodiment, the film layer 22 and the electrolyte layer 24 are together used as the electrochromic composition 27 of the present disclosure. In other embodiments, the electrolyte solution 26 may further include a second oxidizable organic compound (not shown) other than the reducible organic compound 25.

The transparent conductive layers 11, 17, 21, 28 may include transparent substrates and conductive layers. The transparent substrate may be made of glass or plastic, for example, polyethylene terephthalate, polyethylene naphthalate, polycarbonate, or high temperature resistant plastic. The conductive layer may include indium tin oxide (ITO), antimony- or fluorine-doped tin oxide (FTO), antimony- or aluminum-doped zinc oxide, or tin oxide. The adhesive spacers 12 and 23 may be formed by blending spacer elements with a thermosetting or photochemically curable adhesive agent. Spacer elements may be, for example, small spherules of plastic or glass or certain sand fractions. The thickness of the adhesive spacers 12 and 23 may be between 10 µm and 500 µm, for example, between 50 µm and 300 µm. The distance between the first transparent conductive layer and the second transparent conductive layer may be between 10 µm and 500 µm. If the distance between the transparent conductive layers is too small, current leakage and uneven color changing may occur. If the distance between the transparent conductive layers is too large, the reaction rate becomes slow.

When the electrochromic element is out of power, the original neutral state of the electrochromic composition is transparent. After applying a suitable voltage, the color becomes deeper, and the electrochromic composition changes from transparent to a specific color such as gray, dark green, dark blue black, or black because of the complementary effect of the colors produced by the oxidizable polymers and reducible organic compounds. Once the power is turned off, the electrochromic composition is restored to the original transparent state in a short period of time (less than 3 seconds). Compared to those using single oxidizable polymer as the electrochromic compound, the color-changing effect may be achieved by a lower driving voltage and in a shorter time. Also, the optical contrast is improved and makes the color-changing state appear truly black.

Below, exemplary embodiments will be described in detail with reference to the accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

Preparation of Diamine Monomers

The following diamine monomers were prepared in accordance with the synthetic methods described in J. Polym. Sci. Part A: Polym. Chem. 2006, 44, pp4579-4592 and J. Mater. Chem. 2011, 21, 6230-6237.

Diamine monomer (1): triphenylamine (TPA) containing methoxy group (the structure represented by Formula 1, wherein $Ar^1$ is Formula 3, R is —$OCH_3$);

Diamine monomer (2): N,N,N',N'-tetraphenyl-p-phenylenediamine (TPPA) containing methoxy group (the structure represented by Formula 2, wherein $Ar^2$ is Formula 9, R is —$OCH_3$); and Diamine monomer (3): N,N,N',N'-tetraphenylbenzidine (TPB) containing methoxy group (the structure represented by Formula 2, wherein $Ar^1$ is Formula 10, R is —$OCH_3$).

Preparation of Viologen 50 g of 4,4'-bipyridine was dissolved in 500 g of acetonitrile, and then 115 g of heptyl bromide was added. A heating reflux reaction was performed for 18 hours. Then, the golden precipitation was filtered, dried, and crystallized in ethanol to obtain $HVBR_2$. 10.00 g of $HVBR_2$ was dissolved in 100 mL of deionized water, mixed with 100 mL of saturated $NaBF_4$ aqueous solution to produce white solid precipitation of heptyl viologen tetrafluoroborate ($HV(BF_4)_2$). Then, after filtration, it was recrystallized in ethanol to white flake crystals.

Preparation Example A1 (Diamine Monomer (1)+Dicarboxylic Acid to Form Polyamine)

305.37 mg (1.0 mmol) of diamine monomer (1), 258.23 mg (1.0 mmol) of 4,4'-oxydibenzoic acid, and 100 mg of calcium chloride were added to 0.8 mL of triphenyl phosphite, 0.4 mL of pyridine, and 2.0 mL of N-methylpyrrolidone (NMP), heated at 105° C. and stirred for 3 hours. The resulting polymer solution was slowly poured into 300 mL of methanol, stirred and filtered to collect the tough fibrous precipitation. Then, it was fully washed with hot water and methanol and dried at 100° C. under vacuum. The polymer was dissolved by using dimethylacetamide (DMAc) and then precipitated in methanol. This step was repeated twice to finish the purification. The resulting product was called TPA-O for short.

Preparation Example A2 (Diamine Monomer (2)+Dicarboxylic Acid to Form Polyamine)

The same process as in Preparation Example A1 was repeated, except that diamine monomer (1) was replaced by diamine monomer (2): (N,N'-bis(4-aminophenyl)-N,N'-di(4-methoxylphenyl)-1,4-phenylenediamine). The resulting product was called TPPA-O for short.

Preparation Example A3 (Diamine Monomer (2)+Dicarboxylic Acid to Form Polyamine)

The same process as in Preparation Example A1 was repeated, except that diamine monomer (1) was replaced by diamine monomer (3): (N,N'-bis(4-aminophenyl)-N,N'-di(4-methoxyphenyl)-4,4'-biphenyldiamine). The resulting product was called TPB-O for short.

Preparation Example A4 (Copolymer of Polyamine)

A similar process as in Preparation Example A1 was repeated, except that diamine monomer (2) and diamine monomer (3) were used in the same ratio (TPPA:TPB=1:1). 251.31 mg (0.5 mmol) of diamine monomer (2), 289.35 mg (0.5 mmol) of diamine (3), 258.23 mg (1.0 mmol) of 4,4'-oxydibenzoic acid, and 100 mg of calcium chloride were added to 0.8 mL of triphenyl phosphite. 0.4 mL of pyridine, and 2.0 mL of N-methylpyrrolidone (NMP), heated at 105° C. and stirred for 3 hours. The resulting polymer solution was slowly poured into 300 mL of methanol, stirred and filtered to collect the tough fibrous precipitation. Then, it was fully washed with hot water and methanol and dried at 100° C. under vacuum. The polymer was dissolved by using dimethylacetamide (DMAc) and then precipitated in methanol. This step was repeated twice to finish the purification. The resulting product was called TPPA-TPB-O for short.

Preparation Example B1 (Diamine Monomer (1)+Diacyl Chloride to Form Polyamine)

305.4 mg of diamine monomer (1): 4,4'-diamino-4''-methoxytriphenylamine was dissolved in 3.0 mL of DMAc, stirred and cooled to −20° C. in an ice-acetone bath. Then, 0.40 mL of propylene oxide was added to the mixture. 183.0 mg (1.0 mmol) of hexanedioyl dichloride was added to the mixture. Then, the mixture was stirred at −10° C. for 1 hour, then stirred at room temperature for 2 hours. The resulting polymer solution was poured into 400 mL of methanol. The precipitated polymer was filtered, collected, and dried at 100° C. The polymer was dissolved by using DMAc and then precipitated in methanol. This step was repeated twice to finish the purification. The resulting product was called TPA-A for short.

Preparation Example B2 (Diamine Monomer (2)+Diacyl Chloride to Form Polyamine)

The same process as in Preparation Example B1 was repeated, except that diamine monomer (1) was replaced by diamine monomer (2): (N,N'-bis(4-aminophenyl)-N,N'-di(4-methoxylphenyl)-1,4-phenylenediamine). The resulting product was called TPPA-A for short.

Preparation Example B3 (Diamine Monomer (3)+Diacyl Chloride to Form Polyamine)

The same process as in Preparation Example B1 was repeated, except that diamine monomer (1) was replaced by diamine monomer (3): (N,N'-bis(4-aminophenyl)-N,N'-di(4-methoxyphenyl)-4,4'-biphenyldiamine). The resulting product was called TPB-A for short.

Preparation Example B4 (Copolymer of Polyamine)

A similar process as in Preparation Example B1 was repeated, except that diamine monomer (2) and diamine monomer (3) were used in the same ratio (TPPA:TPB=1:1). 251.31 mg (0.5 mmol) of diamine monomer (2) and 289.35 mg (0.5 mmol) of diamine monomer (3) were stirred and cooled to −20° C. in an ice-acetone bath. Then, 0.40 mL of propylene oxide was added to the mixture. 183.0 mg (1.0 mmol) of hexanedioyl dichloride was added to the mixture. Then, the mixture was stirred at −10° C. for 1 hour, then stirred at room temperature for 2 hours. The resulting polymer solution was poured into 400 mL of methanol. The precipitated polymer was filtered, collected, and dried at 100° C. The polymer was dissolved by using DMAc and then precipitated in methanol. This step was repeated twice to finish the purification. The resulting product was called TPPA-TPB-A for short.

Preparation Example C1 (Diamine Monomer (1)+Dianhydride to Form Polyimide)

577 mg of diamine monomer (1) and 424 mg of hydrogenated pyromellitic dianhydride were mixed in a reaction bottle. 2.33 g of NMP was used as solvent and added into the reaction bottle. 20 mg of isoquinoline catalyst was added into the reaction bottle and mixed evenly. The mixture was heated to 210° C. and reacted for 4 hours to obtain a yellow viscous solution. The resulting polymer solution was poured in to 300 mL of methanol. The precipitated polymer was filtered, collected, and dried at 100° C. The polymer was dissolved by using DMAc and then precipitated in methanol. This step was repeated twice to finish the purification. The resulting product was called TPA-I for short.

Preparation Example C2 (Copolymer of Polyimide)

428 mg of diamine monomer (1), 246 mg of 2,2-bis[4(4-aminophenoxy) phenyl]propane, and 496 mg of bicyclo[2.2.2]oct-7-ene-2,3,5,6-tetracarboxylic dianhydride were mixed in a reaction bottle. 2.73 g of NMP was used as solvent and added into the reaction bottle. 20 mg of isoquinoline catalyst was added into the reaction bottle and mixed evenly. The mixture was heated to 210° C. and reacted for 4 hours to obtain a yellow viscous solution. The resulting polymer solution was poured in to 300 mL of methanol. The precipitated polymer was filtered, collected, and dried at 100° C. The polymer was dissolved by using DMAc and then precipitated in methanol. This step was repeated twice to finish the purification. The resulting product was called TPA-C for short.

The products of the above Preparation Examples A1~A4, Preparation Examples B1~B4, Preparation Examples C1~C2 were coated on ITO glass substrates, baked to form a thin film with a thickness of 1 μm. An electrolyte gel with 0.1 M of tetrabutylammonium perchlorate (TBAP)/$CH_3CN$ was coated on the above thin film. Viologen was independently dissolved in 0.1 M of tetrabutylammonium perchlorate (TBAP)/$CH_3CN$. The electrolyte gel mixed with viologen was coated on the ITO glass substrate and baked to form a thin film with a thickness of 1 μm. Voltage was applied to each of the aforementioned film layers and the optical absorption spectrum was measured (not shown). The redox potentials obtained according to the optical absorption spectrum are shown in Table 1.

TABLE 1

| | First oxidation potential (V) | Second oxidation potential (V) |
|---|---|---|
| Viologen | −0.42 (blue) | −0.84 (blue purple) |
| Preparation Example A1 | 0.95 (green) | — |
| Preparation Example A2 | 0.75 (green) | 1.10 (blue) |
| Preparation Example A3 | 0.80 (red) | 1.05 (blue) |
| Preparation Example A4 | 0.75 (green) | 0.80 (brown black) |
| Preparation Example B1 | 0.95 (green) | — |
| Preparation Example B2 | 0.75 (green) | 1.00 (blue) |
| Preparation Example B3 | 0.80 (red) | 1.05 (blue) |
| Preparation Example B4 | 0.75 (red) | 0.80 (brown black) |
| Preparation Example C1 | 1.25 (dark blue) | — |
| Preparation Example C2 | 1.25 (blue) | — |

According to the experiments, it can be found that viologen and all of the polyamide (Preparation Examples A1~A4 and Preparation Examples B1~B4) were transparent and colorless in the neutral state (0V). However, when in the oxidation state (the applied voltage was increased), the absorption significantly changed at a specific wavelength, and revealed the specific spectral absorption characteristics of each polyamide. When the first redox potential was applied, viologen was at a reduced state and was blue. Polyamides (Preparation Example A2 (TPPA-O) and Preparation Example B2 (TPPA-A)) using TPPA units have a stronger absorption peak at the wavelengths near the blue light region 430 nm and red light region 600 nm of the visible light region, making the thin film change to green at the first redox potential. When the voltage was further increased to the second oxidation potential, a new absorption peak appeared at 835 nm, and the color of the thin film changed from green to blue. Polyamides (Preparation Example A3 (TPB-O) and Preparation Example B3 (TPB-A)) revealed a strong absorption peak at 486 nm, making the color of the thin film turn red. When the voltage was further increased to the second oxidation potential, the color of the thin film changed from red to blue. The main difference between the two chromophores is mainly because of the conjugation length. Compared to TPPA-polyamide, TPB-polyamides have one more benzene ring, resulting in a red shift. Therefore, by using the significantly different absorption range of these two polyamides (TPPA-PA and TPB-PA), color control can be effectively performed in the visible light region.

Figure 2:
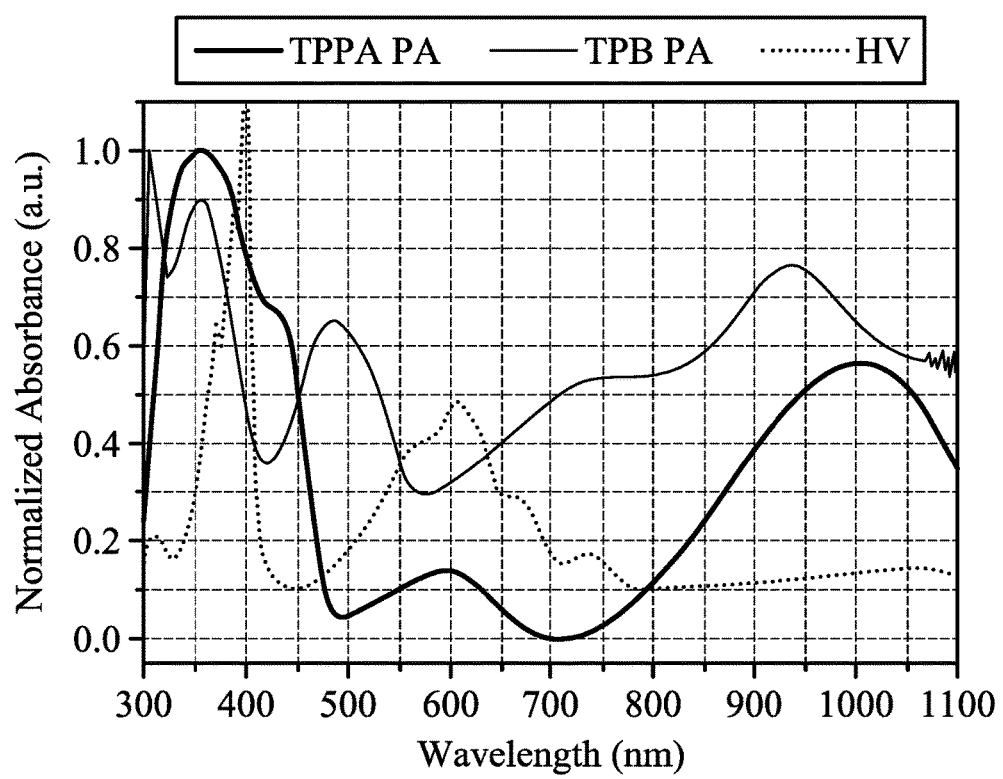
FIG. 2 illustrates the overlapping absorption spectrum of each component of the electrochromic composition in accordance with an embodiment of the present disclosure.

FIG. 2 illustrates the overlapping absorption spectrum of each component of the electrochromic composition. Referring to FIG. 2, it can be observed that the working potentials and the characteristic absorption peaks of the oxidized polyamide (Preparation Example B2 (TPPA-A) and Preparation Example B3 (TPB-A), for example) and reduced organic compound (viologen; HV) can be successively matched and reveal an excellent complementary color effect. When overlapping the absorption spectra of the Preparation Example B2 (TPPA-A) (first oxidation state is green), Preparation Example B3 (TPB-A) (first oxidation state is red), and viologen (HV) (first reduced state is blue), the absorption range can almost completely cover the whole visible light region. There is a good shielding effect in the visible light region.

Because the electrochemical behaviors of the polyamides derived from aromatic and aliphatic dicarboxylic acid are similar, the following Comparative Examples 1~2 and Examples 1~2 use aromatic polyamide (the product of Preparation Example A2 (TPPA-O) and the product of Preparation Example A3 (TPB-O)) as examples for explanation. At first, the aforementioned products were used to manufacture electrochromic elements. Then, the cyclic voltammetry (CV) spectrum of the electrochromic composition in the electrochromic element was measured.

Electrochromic Element

Comparative Example 1 (TPPA-O without Viologen)

The product of Preparation Example A2 (TPPA-O) was prepared in DMAc to form a solution with a concentration of 10 (mg/mL). 300 μL of the solution was dropped and coated on the effective area (25 mm×20 mm) of ITO glass substrate (20 mm×30 mm×1 mm, 5Ω/□), and then dried under vacuum to prepare a film with a thickness of 1 μm. The distance between two electrodes was defined by an adhesive spacer frame with a thickness of 50 μm. 1.25 g of polymethylmethacrylate (PMMA) (molecular weight: 120, 000) and 0.15 g of LiBF$_4$ were dissolved in 2.75 g of propylene carbonate (PC) to form an electrolyte gel of 0.7 M. The electrolyte gel was coated on one side of the aforementioned film layer, and then clasped between the two electrodes (the material of the electrode is ITO glass substrate), and sealed by PI tapes or quick-drying epoxy resins to obtain the electrochromic element.

Figure 3A:
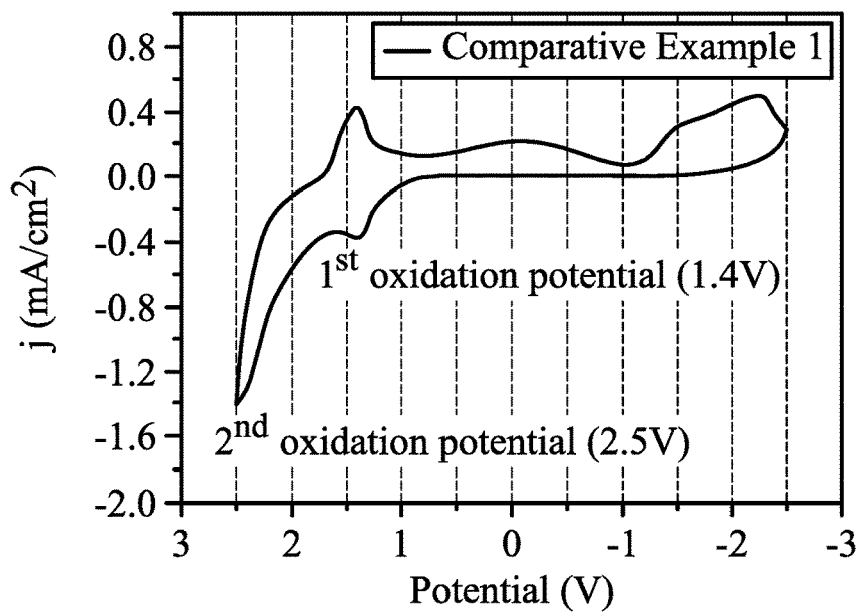
FIG. 3A illustrates the cyclic voltammetry spectrum of the electrochromic composition in accordance with some examples of the present disclosure.

The cyclic voltammetry (CV) spectra of the electrochromic composition in the aforementioned electrochromic element are shown in FIG. 3A.

Example 1 (TPPA-O with Viologen)

The product of Preparation Example A2 (TPPA-O) was prepared in DMAc to form a solution with a concentration of 10 (mg/mL). 300 µL of the solution was dropped and coated on the effective area (25 mm×20 mm) of ITO glass substrate (20 mm×30 mm×1 mm, 5Ω/□), and then dried under vacuum to prepare a film with a thickness of 1 µm. The distance between two electrodes was defined by an adhesive spacer frame with a thickness of 50 µm. 1.25 g of polymethylmethacrylate (PMMA) (molecular weight: 120,000) was dissolved in 2.75 g of propylene carbonate (PC), then 0.15 g of LiBF$_4$ and 0.06 g of viologen (HV(BF$_4$)$_2$) were mixed to form an electrolyte gel of 0.05 M. The electrolyte gel was coated on one side of the aforementioned film layer, and then clasped between the two electrodes (the material of the electrode is ITO glass substrate), and sealed by PI tapes to obtain the electrochromic element.

Figure 3B:
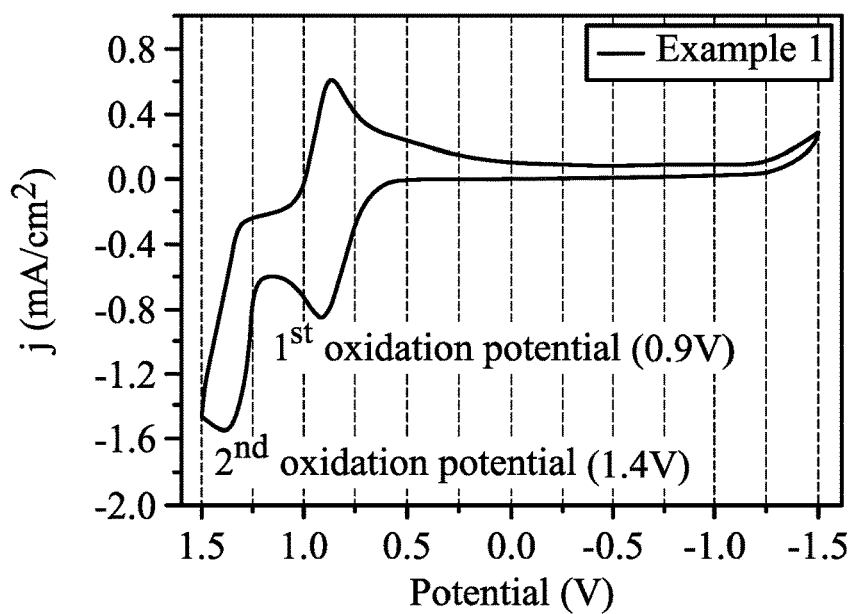
FIG. 3B illustrates the cyclic voltammetry spectrum of the electrochromic composition in accordance with some examples of the present disclosure.

The cyclic voltammetry (CV) spectra of the electrochromic composition in the aforementioned electrochromic element are shown in FIG. 3B.

Comparative Example 2 (TPB-O without Viologen)

The product of Preparation Example A3 (TPB-O) was prepared in DMAc to form a solution with a concentration of 10 (mg/mL). 300 µL of the solution was dropped and coated on the effective area (25 mm×20 mm) of ITO glass substrate (20 mm×30 mm×1 mm, 5Ω/□), and then dried under vacuum to prepare a film with a thickness of 1 µm. The distance between two electrodes was defined by an adhesive spacer frame with a thickness of 50 µm. 1.25 g of polymethylmethacrylate (PMMA) (molecular weight: 120,000) and 0.15 g of LiBF$_4$ were dissolved in 2.75 g of propylene carbonate (PC) to form an electrolyte gel of 0.7 M. The electrolyte gel was coated on one side of the aforementioned film layer, and then clasped between the two electrodes (the material of the electrode is ITO glass substrate), and sealed by PI tapes to obtain the electrochromic element.

Figure 4A:
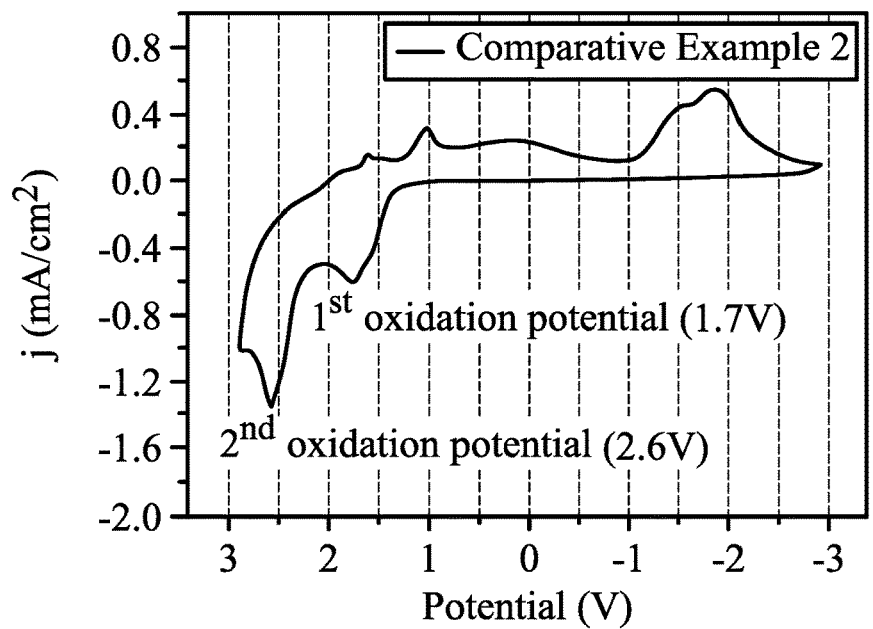
FIG. 4A illustrates the cyclic voltammetry spectrum of the electrochromic composition in accordance with some other examples of the present disclosure.

The cyclic voltammetry (CV) spectra of the electrochromic composition in the aforementioned electrochromic element are shown in FIG. 4A.

Example 2 (TPB-O with Viologen)

The product of Preparation Example A3 (TPB-O) was prepared in DMAc to form a solution with a concentration of 10 (mg/mL). 300 µL of the solution was dropped and coated on the effective area (25 mm×20 mm) of ITO glass substrate (20 mm×30 mm×1 mm, 5Ω/□), and then dried under vacuum to prepare a film with a thickness of 1 µm. The distance between two electrodes was defined by an adhesive spacer frame with a thickness of 50 µm. 1.25 g of polymethylmethacrylate (PMMA) (molecular weight: 120,000) was dissolved in 2.75 g of propylene carbonate (PC), then 0.15 g of LiBF$_4$ and 0.06 g of viologen (HV(BF$_4$)$_2$) were mixed to form an electrolyte gel of 0.05 M. The electrolyte gel was coated on one side of the aforementioned film layer, and then clasped between the two electrodes (the material of the electrode is ITO glass substrate), and sealed by PI tapes to obtain the electrochromic element.

Figure 4B:
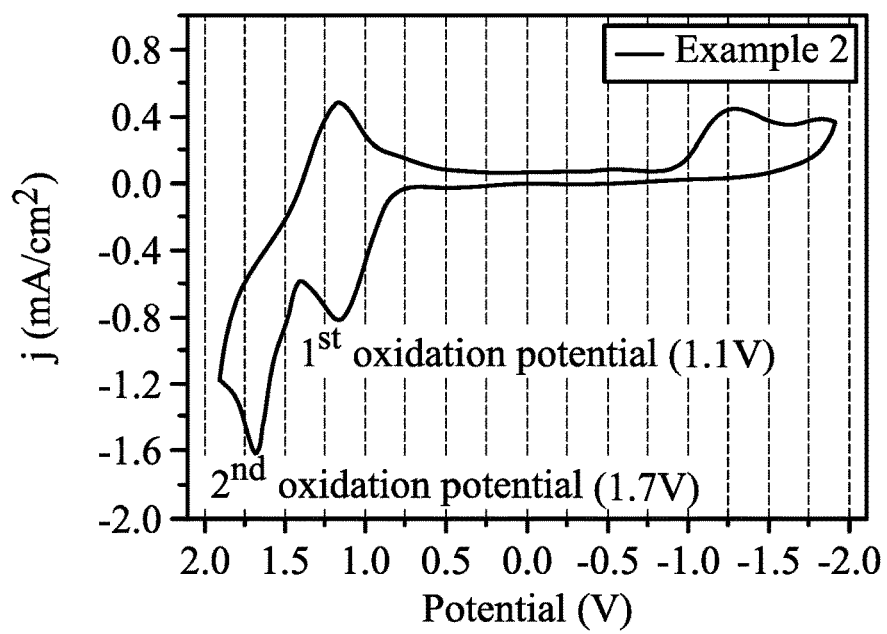
FIG. 4B illustrates the cyclic voltammetry spectrum of the electrochromic composition in accordance with some other examples of the present disclosure.

The cyclic voltammetry (CV) spectra of the electrochromic composition in the aforementioned electrochromic element are shown in FIG. 4B.

It can be found by comparing FIG. 3A and FIG. 3B that while 1.4 V of driving voltage was required in Comparative Example 1, the driving voltage required in Example 1 decreased to 0.9 V. It can be found by comparing FIG. 4A and FIG. 4B that while 1.7 V of driving voltage was required in Comparative Example 2, the driving voltage required in Example 2 decreased to 1.1 V. This reveals that the driving may be performed by using a lower oxidation potential because of the introduction of viologen (HV(BF$_4$)$_2$). The effect can be achieved because viologen can effectively capture electrons. Therefore, the working potential can be significantly reduced, and the overall performance of the electrochromic element is improved.

Example 3 (TPPA-TPB-O Copolymer with Viologen)

The product of Preparation Example A4 (TPPA-TPB-O) was prepared in DMAc to form a solution with a concentration of 10 (mg/mL). 300 µL of the solution was dropped and coated on the effective area (25 mm×20 mm) of ITO glass substrate (20 mm×30 mm×1 mm, 5Ω/□), and then dried under vacuum to prepare a film with a thickness of 250 nm. The distance between two electrodes was defined by an adhesive spacer frame with a thickness of 50 µm. 1.25 g of polymethylmethacrylate (PMMA) (molecular weight: 120,000) was dissolved in 2.75 g of propylene carbonate (PC), then 0.15 g of LiBF$_4$ and 0.06 g of viologen (HV(BF$_4$)$_2$) were mixed to form an electrolyte gel of 0.05 M. The electrolyte gel was coated on one side of the aforementioned film layer, and then clasped between the two electrodes (the material of the electrode is ITO glass substrate), and sealed by PI tapes to obtain the electrochromic element.

Example 4 (Mixture of TPPA-O and TPB-O with Viologen)

The product of Preparation Example A2 (TPPA-O) and the product of Preparation Example A3 (TPB-O) were prepared in DMAc to form a solution with a concentration of 10 (mg/mL). 300 µL of the solution was dropped and coated on the effective area (25 mm×20 mm) of ITO glass substrate (20 mm×30 mm×1 mm, 5Ω/□), and then dried under vacuum to prepare a film with a thickness of 250 nm. The distance between two electrodes was defined by an adhesive spacer frame with a thickness of 50 µm. 1.25 g of polymethylmethacrylate (PMMA) (molecular weight: 120,000) was dissolved in 2.75 g of propylene carbonate (PC), then 0.15 g of LiBF$_4$ and 0.06 g of viologen (HV(BF$_4$)$_2$) were mixed to form an electrolyte gel of 0.05 M. The electrolyte gel was coated on one side of the aforementioned film layer, and then clasped between the two electrodes (the material of the electrode is ITO glass substrate), and sealed by PI tapes to obtain the electrochromic element.

Example 5 (Mixture of TPPA-O and TPB-O with Viologen)

The same process as in Example 4 was repeated, except that the thickness of the film formed by the product of Preparation Example A2 (TPPA-O) and the product of Preparation Example A3 (TPB-O) was increased to 1000 nm.

Example 6 (Mixture of TPPA-A and TPB-A with Viologen)

The same process as in Example 4 was repeated, except that the product of Preparation Example A2 (TPPA-O) and the product of Preparation Example A3 (TPB-O) were replaced by the mixed solution of the product of Preparation Example B2 (TPPA-A) and the product of Preparation Example B3 (TPB-A). Also, the thickness of the film formed thereof was increased to 1000 nm.

Figure 5:
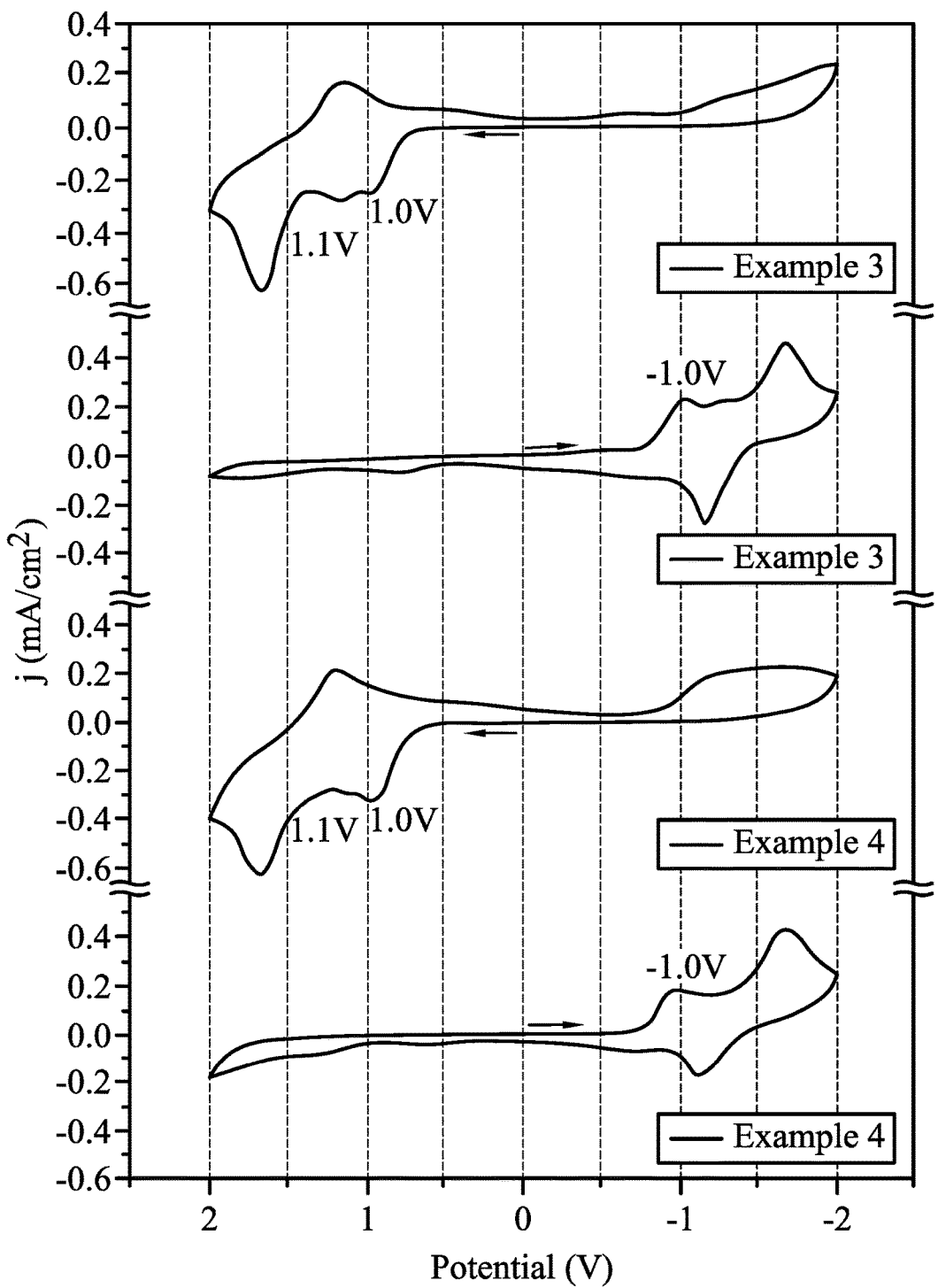
FIG. 5 illustrates the cyclic voltammetry spectrum of the electrochromic composition in accordance with some embodiments of the present disclosure.

FIG. 5 illustrates the cyclic voltammetry spectrum of the electrochromic compositions of Example 3 and Example 4. It can be observed from the CV curve shown in FIG. 5 that Example 3 and Example 4 have similar reversible redox behavior, the oxidation potential of Example 3 (TPPA-TPB-O copolymer) was 1.0 V and 1.1V, the oxidation potential of Example 4 (a mixture of TPPA-O and TPB-O) was 1.0 V and 1.1 V, confirming the electroactive unit was successively included.

Figure 6A:
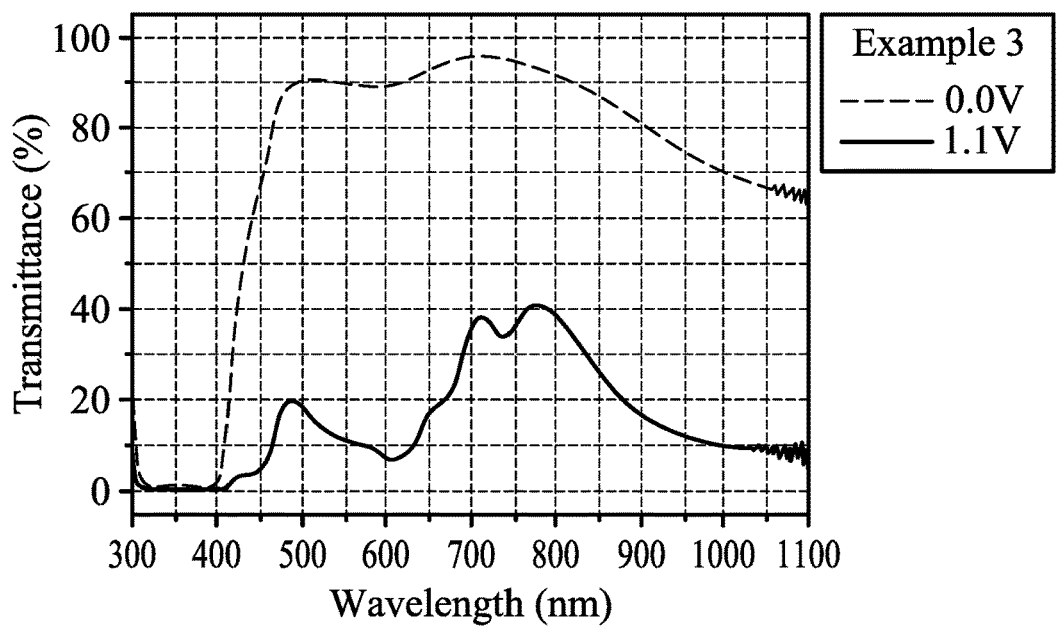
FIG. 6A illustrates the transmission spectrum of the electrochromic composition in accordance with some embodiments of the present disclosure.
Figure 6B:
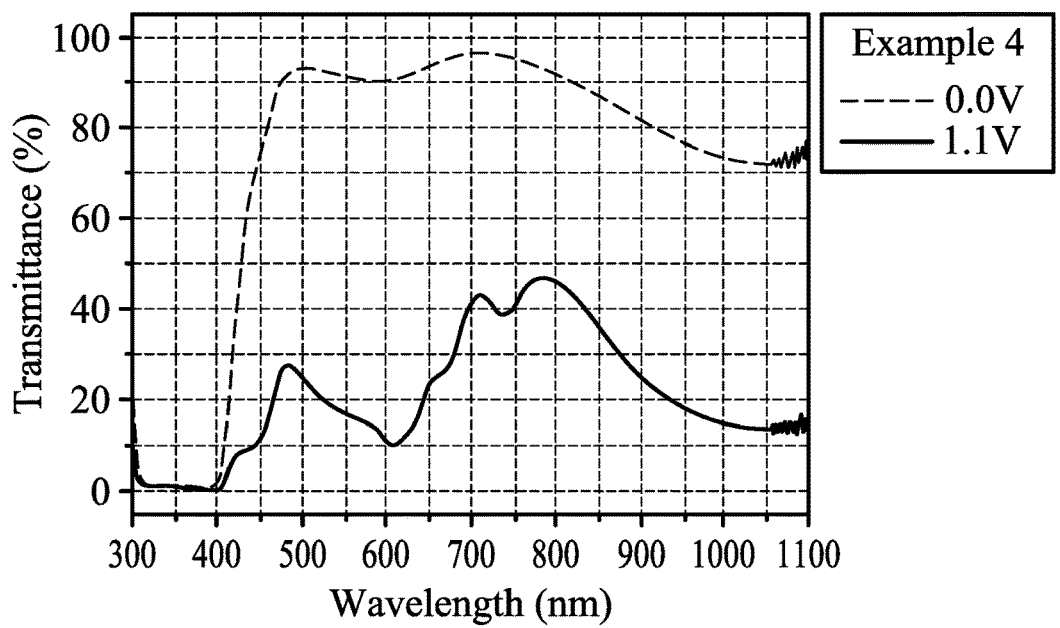
FIG. 6B illustrates the transmission spectrum of the electrochromic composition in accordance with some embodiments of the present disclosure.

FIG. 6A illustrates the transmission spectrum of the electrochromic composition of Example 3. FIG. 6B illustrates the transmission spectrum of the electrochromic composition of Example 4. It can be observed by comparing FIG. 6A and FIG. 6B that the two electrochromic compositions in Example 3 and Example 4 were in a neutral state when no voltage was applied (0.0 V) and have high transmittance, the device was colorless and transparent with good transparency. When the voltage was increased to 1.1 V, it turned to be in an oxidation state (colored state) and to have low transmittance. The device appeared to be black, representing that the oxidizable polymers and reducible organic compounds in the electrochromic composition closely match each other under a redox potential (1.1 V). Therefore, the feature of color overlapping was obtained and a complementary effect of the colors was produced.

Figure 7:
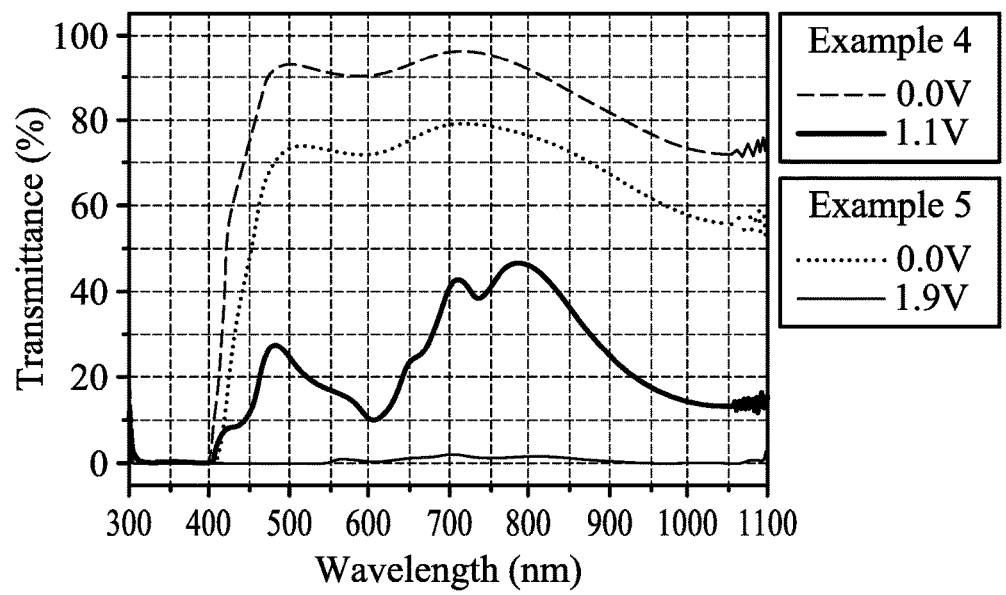
FIG. 7 illustrates the transmission spectrum of the electrochromic composition in accordance with some embodiments of the present disclosure.

FIG. 7 illustrates the transmission spectrum of the electrochromic compositions of Example 4 and Example 5. It can be observed from FIG. 7 that Example 4 (film thickness was 250 nm) was in a neutral state when no voltage was applied (0.0 V), the device was colorless and transparent with good transparency. When the voltage was increased to 1.1 V, it turned to be in an oxidation state (colored state) and the transmittance in the absorption band of the whole visible light region and near infrared region (800~1100 nm) decreased. The device appeared to be dark green, but not yet a truly black. In comparison, Example 5 (film thickness was 1000 nm) was in a neutral state when no voltage was applied (0.0 V) the device was colorless and transparent with good transparency. When the voltage was increased to 1.9 V, it turned to be in an oxidation state (colored state) and the whole transmittance decreased significantly, the device appeared to be truly black. It can be learned that appropriately increasing the thickness of the film is beneficial to making the oxidation state (colored state) to appear as truly black.

Figure 8:
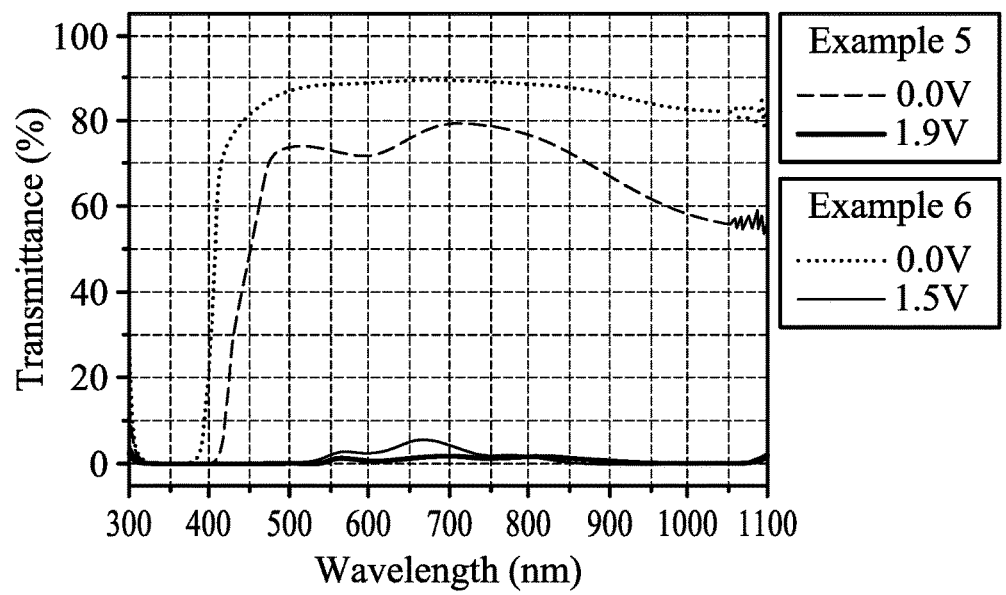
FIG. 8 illustrates the transmission spectrum of the electrochromic composition in accordance with some embodiments of the present disclosure.

FIG. 8 illustrates the transmission spectrum of the electrochromic compositions in Example 5 and Example 6. In can be observed from FIG. 8 that the overall transmittance of Example 5 and Example 6 was decreased significantly while in an oxidation state, and the device may appear as truly black. Also, when Example 6 was in a neutral state, the transmittance was enhanced to over 80%, further enhancing the transparency of the device.

Figure 9:
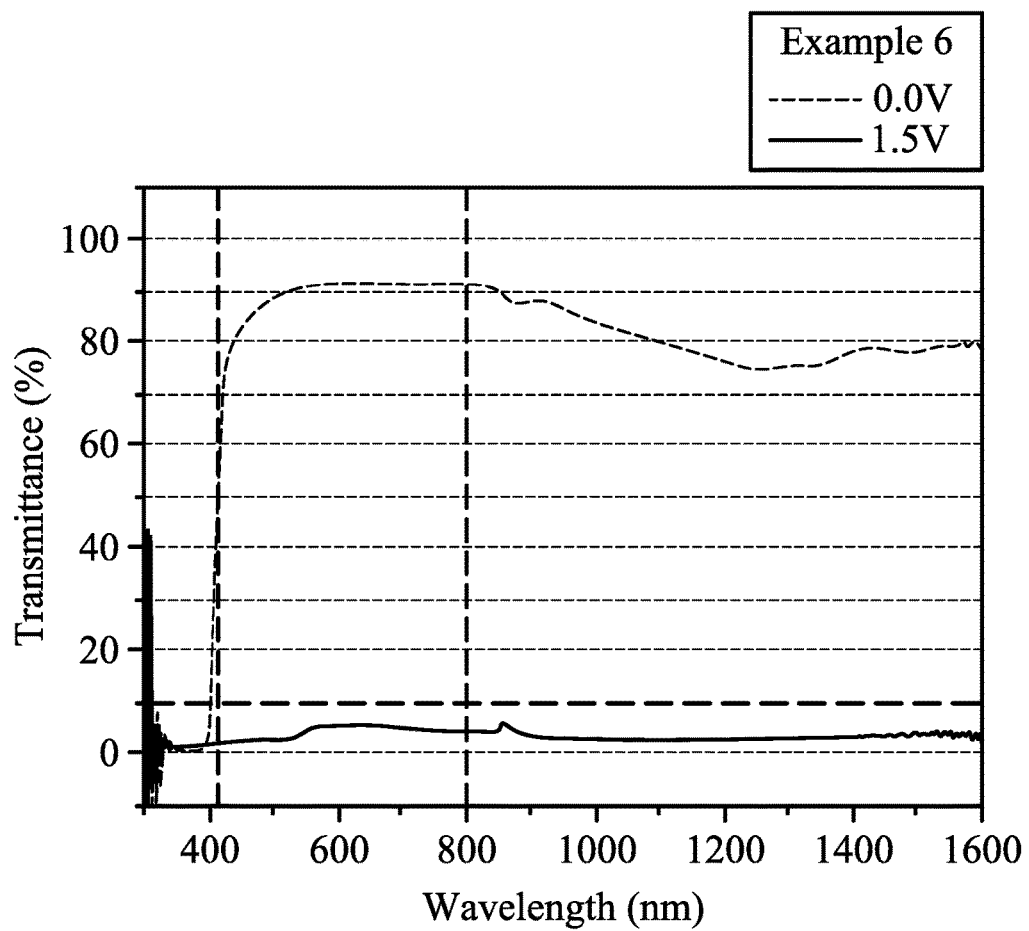
FIG. 9 illustrates the transmission spectrum of the electrochromic composition in accordance with some embodiments of the present disclosure.

FIG. 9 illustrates the transmission spectrum of the electrochromic composition of Example 6. The change of transmittance between the visible region and the near infrared region can be observed from FIG. 9. From a high transparency (T>85%) of the neutral state to a truly black (T<6%) of the oxidation state (colored state), it has a good optical contrast (Δ T). In addition, according to the data obtained from the colorimeter, when the electrochromic element of Example 6 was in a neutral state, the CIE 1976 chromaticity coordinates were L*: 96.8, a*: −2.0, b*: 5.3, and when the electrochromic element of Example 6 was in an oxidation state, the CIE 1976 chromaticity coordinates were L*: 8.6, a*: −4.0, b*: 5.0. The change of L* is greater than 79% (88.2 ΔL*), illustrating that the neutral state of the electrochromic element of Example 6 is transparent and the oxidation state (colored state) thereof is truly black.

The electrochromic composition provided by the present disclosure has a low driving voltage, electrochromic stability, and a high potential for application in transparent displays and related optical devices. In addition, the electrochromic composition provided by the present disclosure can have a high transparency in a neutral state, and the transmittance of the redox state can be decreased by the color complementarity produced by the oxidizable organic polymers and the reducible organic small molecules. Therefore, the electrochromic composition can have a deeper color, or even have a truly black color.

While the invention has been described by way of example and in terms of the preferred embodiments, it is to be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An electrochromic composition, comprising:
   0.5~10 parts by weight of a first oxidizable polymer;
   0.5~10 parts by weight of a reducible organic compound;
   0.5~20 parts by weight of an electrolyte; and
   60~98.5 parts by weight of a solvent,
   wherein the first oxidizable polymer is:
   a polymer of 1 molar part of a diamine and 0.1~20 molar parts of dicarboxylic acid, diacyl chloride, or dianhydride;
   a mixture of polymers of 1 molar part of a diamine and 0.1~20 molar parts of dicarboxylic acid, diacyl chloride, or dianhydride; or
   a copolymer of the polymers,
   wherein the diamine is Formula 1, Formula 2, or a combination thereof:

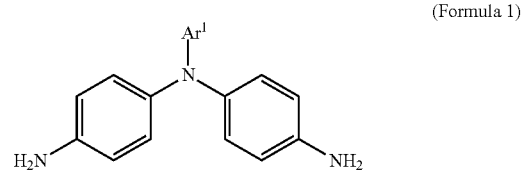

(Formula 1)

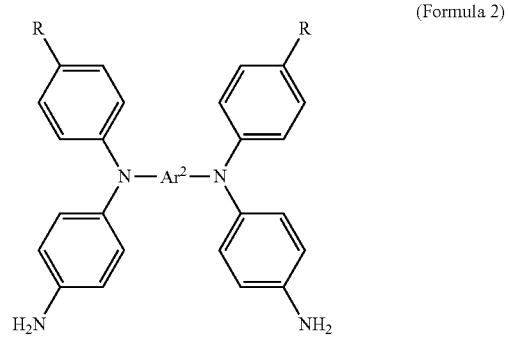

(Formula 2)

Ar¹ is Formula 3, Formula 4, Formula 5, Formula 6, Formula 7, or Formula 8:

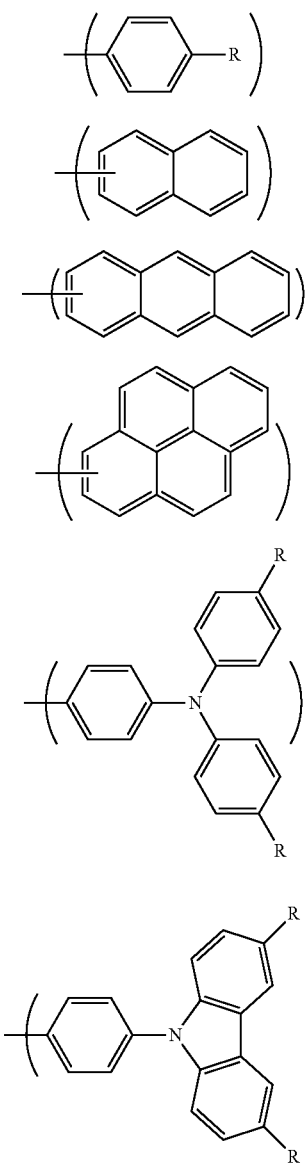

(Formula 3)

(Formula 4)

(Formula 5)

(Formula 6)

(Formula 7)

(Formula 8)

R is —H, —F, —Br, —Cl, —I, —CH₃, —C₂H₅, —C₃H₇, -n-C₄H₉, -s-C₄H₉, -t-C₄H₉, —C₅H₁₁, —C₆H₁₃, —C₇H₁₅, —OCH₃, —OC₂H₅, —OC₃H₇, -n-OC₄H₉, -s-C₄H₉, -t-C₄H₉, —OC₅H₁₁, —OC₆H₁₃, or —OC₇H₁₅;

Ar² is Formula 9, Formula 10, Formula 11, or Formula 12:

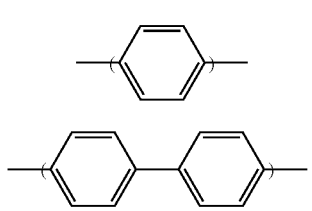

(Formula 9)

(Formula 10)

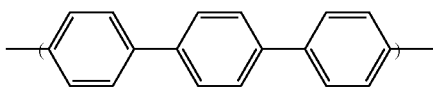

(Formula 11)

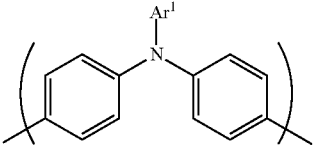

(Formula 12)

wherein the dicarboxylic acid is Formula 13, the diacyl chloride is Formula 14, the dianhydride is Formula 15:

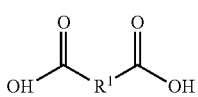

(Formula 13)

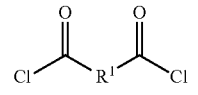

(Formula 14)

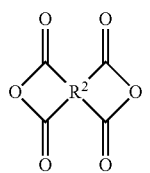

(Formula 15)

R¹ is selected from the group of —(CH₂)ₙ—, Formula 9, Formula 16, Formula 17, Formula 18, Formula 19, Formula 20, Formula 21, Formula 22, Formula 23, and Formula 24, wherein n is between 1 and 12:

(Formula 9)

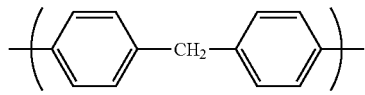

(Formula 16)

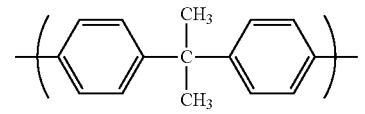

(Formula 17)

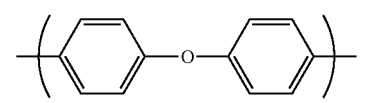

(Formula 18)

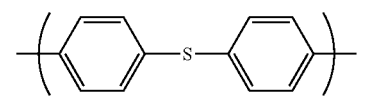

(Formula 19)

(Formula 20)
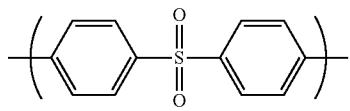

(Formula 21)
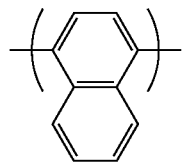

(Formula 22)
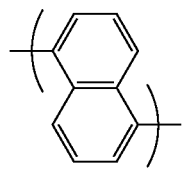

(Formula 23)
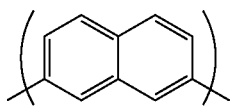

(Formula 24)
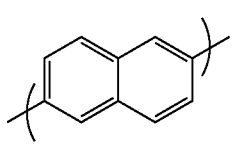

$R^2$ is cyclic aliphatic or organic aromatic.

2. The electrochromic composition as claimed in claim 1, wherein the first oxidizable polymer comprises a polymer of Formula 25, Formula 26, Formula 27, or Formula 28, or a copolymer of the aforementioned polymers:

(Formula 25)
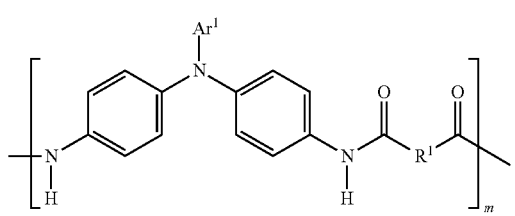

(Formula 26)

(Formula 27)

(Formula 28)
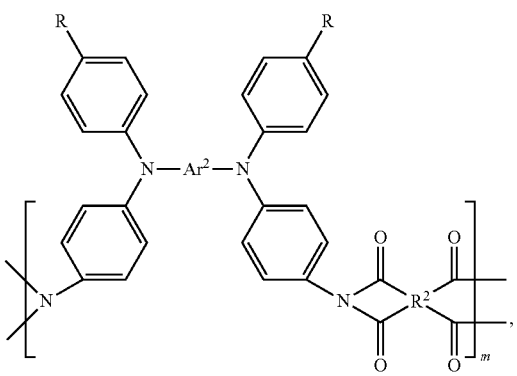

wherein m is between 1 and 300.

3. The electrochromic composition as claimed in claim 2, wherein the copolymer is a copolymer of the polymer of Formula 25, which is represented by Formula 29:

(Formula 29)
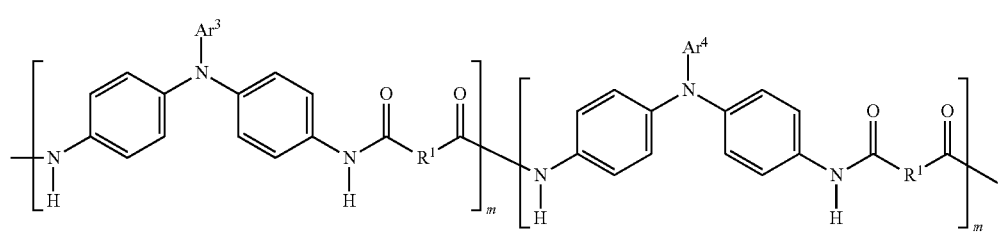

each of Ar³ and Ar⁴ is independently Formula 3, Formula 4, Formula 5, Formula 6, Formula 7, or Formula 8, wherein Ar³ is different from Ar⁴, and m is between 1 and 300.

4. The electrochromic composition as claimed in claim 2, wherein the copolymer is a copolymer of the polymer of Formula 26, which is represented by Formula 30:

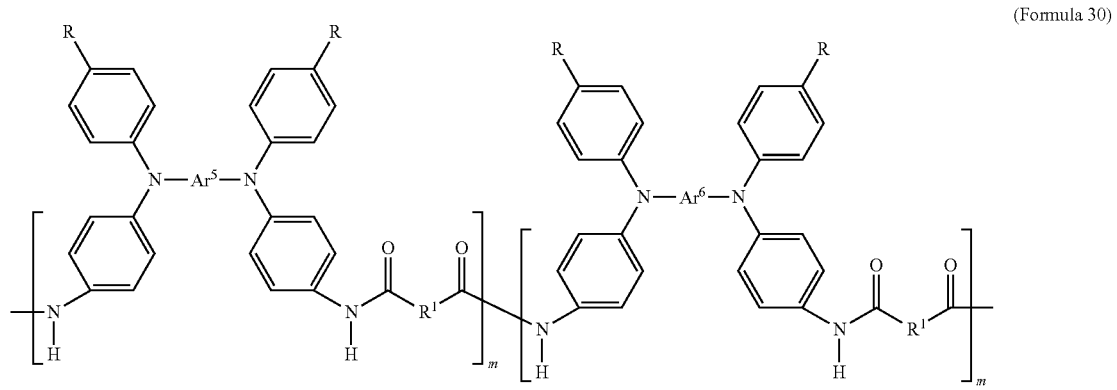

(Formula 30)

each of Ar⁵ and Ar⁶ is independently Formula 9, Formula 10, Formula 11, or Formula 12, wherein Ar⁵ is different from Ar⁶, and m is between 1 and 300.

5. The electrochromic composition as claimed in claim 2, wherein the copolymer is a copolymer of the polymer of Formula 27, which is represented by Formula 31:

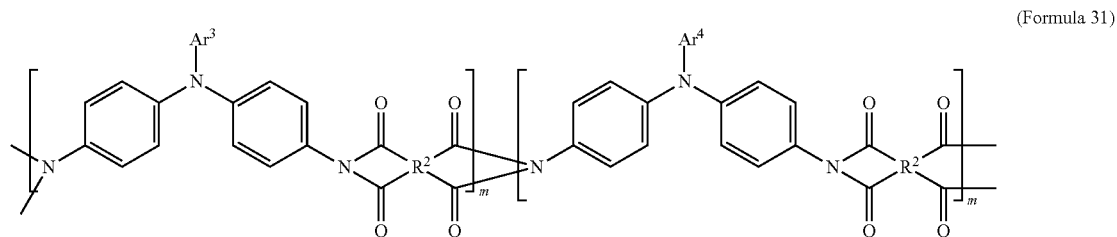

(Formula 31)

each of Ar³ and Ar⁴ is independently Formula 3, Formula 4, Formula 5, Formula 6, Formula 7, or Formula 8, wherein Ar³ is different from Ar⁴, and m is between 1 and 300.

6. The electrochromic composition as claimed in claim 2, wherein the copolymer is a copolymer of the polymer of Formula 28, which is represented by Formula 32:

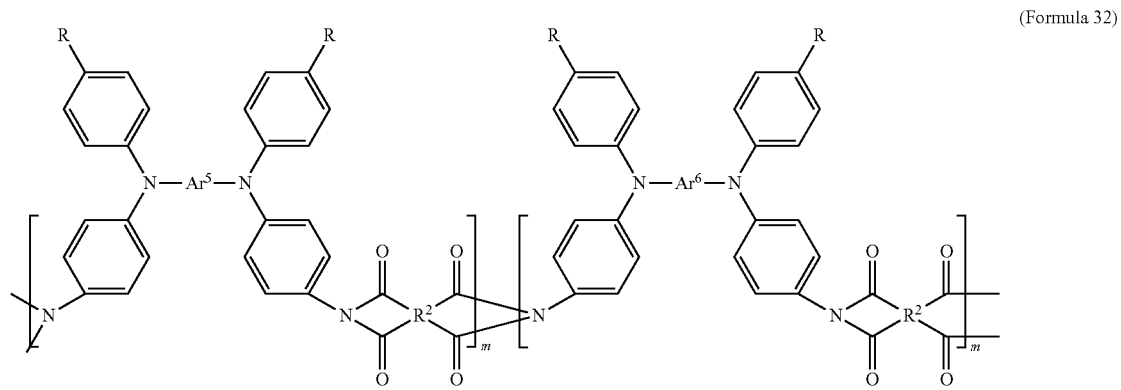

(Formula 32)

each of $Ar^5$ and $Ar^6$ is independently Formula 9, Formula 10, Formula 11, or Formula 12, wherein $Ar^5$ is different from $Ar^6$, and m is between 1 and 300.

7. The electrochromic composition as claimed in claim 1, wherein the diamine is Formula 33, and the dicarboxylic acid is Formula 34 or Formula 35:

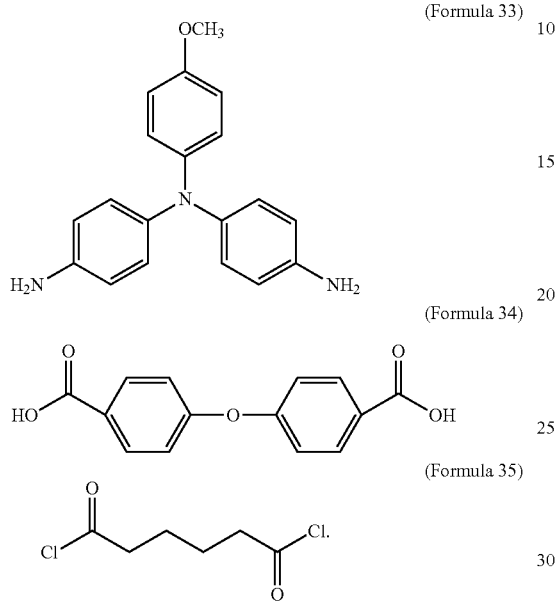

(Formula 33)

(Formula 34)

(Formula 35)

8. The electrochromic composition as claimed in claim 1, wherein the diamine is Formula 36, and the dicarboxylic acid is Formula 34 or Formula 35:

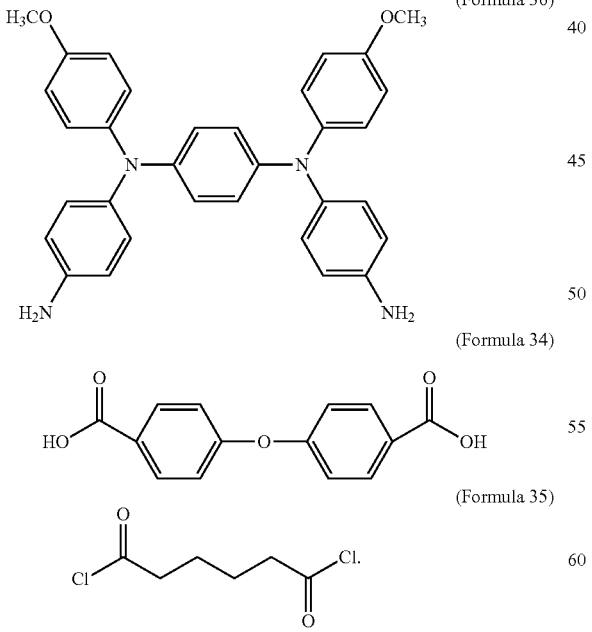

(Formula 36)

(Formula 34)

(Formula 35)

9. The electrochromic composition as claimed in claim 1, wherein the diamine is Formula 37, and the dicarboxylic acid is Formula 34 or Formula 35:

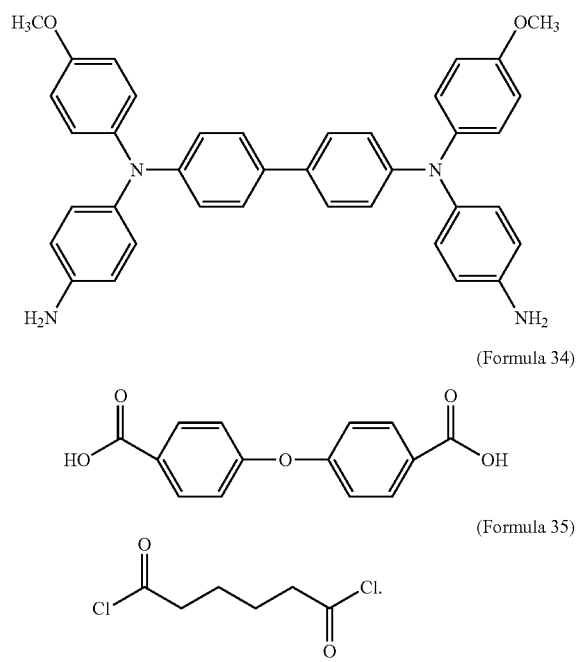

(Formula 37)

(Formula 34)

(Formula 35)

10. The electrochromic composition as claimed in claim 1, wherein the reducible organic compound is Formula 38, Formula 39, Formula 40, a derivative thereof, or a combination thereof:

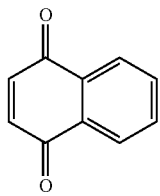

(Formula 38)

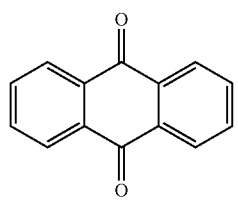

(Formula 39)

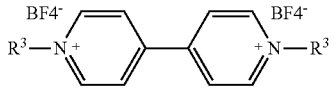

(Formula 40)

wherein $R^3$ is H or $C_1$~$C_{12}$ alkyl.

11. The electrochromic composition as claimed in claim 1, further comprising a second oxidizable organic compound of Formula 41, Formula 42, Formula 43, Formula 44, Formula 45, or a combination thereof:

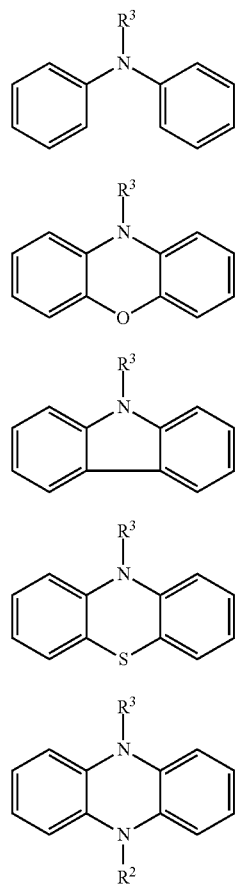

(Formula 41)

(Formula 42)

(Formula 43)

(Formula 44)

(Formula 45)

wherein $R^3$ is H or $C_1$~$C_{12}$ alkyl.

12. The electrochromic composition as claimed in claim 1, wherein the electrolyte is an organic ammonium salt or an inorganic lithium salt, and the concentration of the electrolyte is between 0.01 M and 3.0 M.

13. The electrochromic composition as claimed in claim 1, wherein a molar ratio of the first oxidizable polymer to the electrolyte is between 1:1 and 1:300, and the molar ratio of the reducible organic compound to the electrolyte is between 1:1 and 1:300.

14. The electrochromic composition as claimed in claim 1, wherein a weight average molecular weight of the first oxidizable polymer is between 1,000 and 300,000.

15. The electrochromic composition as claimed in claim 1, wherein the first oxidizable polymer is a film layer.

16. An electrochromic element, comprising:
a first transparent conductive layer;
a second transparent conductive layer disposed opposite to the first transparent conductive layer;
an adhesive spacer, connected to the surfaces of the first transparent conductive layer and the second transparent conductive layer, and the first transparent conductive layer, the second transparent conductive layer, and the adhesive spacer form a cell; and
an electrochromic composition as claimed in claim 1, filled in the cell.

17. The electrochromic element as claimed in claim 16, wherein the electrochromic composition further comprises a second oxidizable organic compound of Formula 41, Formula 42, Formula 43, Formula 44, Formula 45, or a combination thereof:

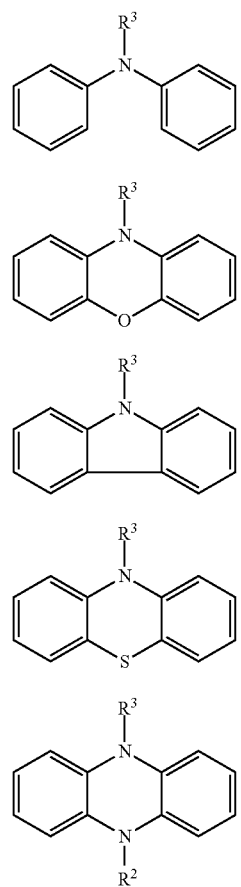

(Formula 41)

(Formula 42)

(Formula 43)

(Formula 44)

(Formula 45)

wherein $R^3$ is H or $C_1$~$C_{12}$ alkyl.

18. The electrochromic element as claimed in claim 16, wherein a distance between the first transparent conductive layer and the second transparent conductive layer is 10 μm~500 μm.

19. An electrochromic element, comprising:
a first transparent conductive layer;
a second transparent conductive layer disposed opposite to the first transparent conductive layer;
a film layer disposed on the first transparent conductive layer and composed of a first oxidizable polymer, said first oxidizable polymer being:
a polymer of 1 molar part of a diamine and 0.1~20 molar parts of dicarboxylic acid, diacyl chloride, or dianhydride;
a mixture of polymers of 1 molar part of a diamine and 0.1~20 molar parts of dicarboxylic acid, diacyl chloride, or dianhydride; or
a copolymer of the polymers,
wherein the diamine is Formula 1, Formula 2, or a combination thereof:

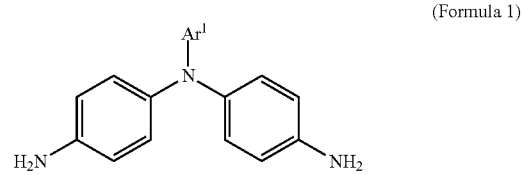

(Formula 1)

-continued (Formula 2)

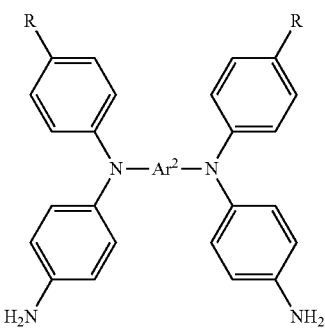

Ar¹ is Formula 3, Formula 4, Formula 5, Formula 6, Formula 7, or Formula 8:

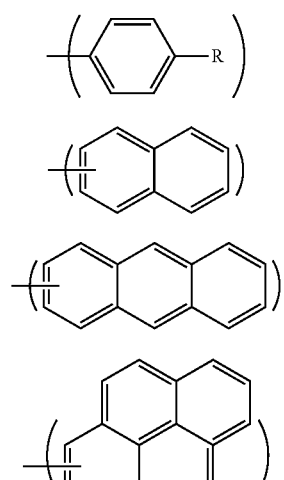

(Formula 3)

(Formula 4)

(Formula 5)

(Formula 6)

(Formula 7)

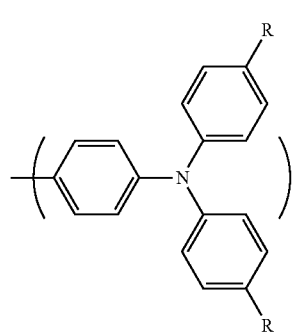

(Formula 8)

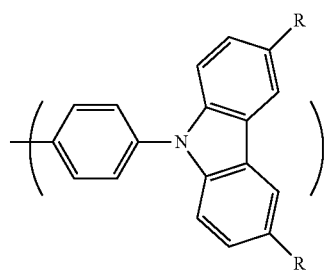

R is —H, —F, —Br, —Cl, —I, —CH$_3$, —C$_2$H$_5$, —C$_3$H$_7$, -n-C$_4$H$_9$, -s-C$_4$H$_9$, -t-C$_4$H$_9$, —C$_5$H$_{11}$, —C$_6$H$_{13}$, —C$_7$H$_{15}$, —OCH$_3$, —OC$_2$H$_5$, —OC$_3$H$_7$, -n-OC$_4$H$_9$, -s-C$_4$H$_9$, -t-C$_4$H$_9$, —OC$_5$H$_{11}$, —OC$_6$H$_{13}$, or —OC$_7$H$_{15}$;

Ar² is Formula 9, Formula 10, Formula 11, or Formula 12:

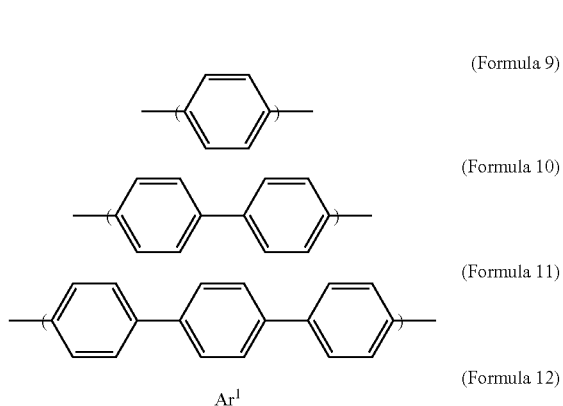

(Formula 9)

(Formula 10)

(Formula 11)

(Formula 12)

wherein the dicarboxylic acid is Formula 13, the diacyl chloride is Formula 14, the dianhydride is Formula 15:

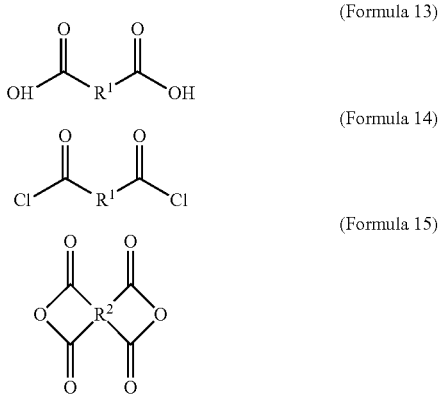

(Formula 13)

(Formula 14)

(Formula 15)

R¹ is selected from the group of —(CH$_2$)$_n$—, Formula 9, Formula 16, Formula 17, Formula 18, Formula 19, Formula 20, Formula 21, Formula 22, Formula 23, and Formula 24, wherein n is between 1 and 12:

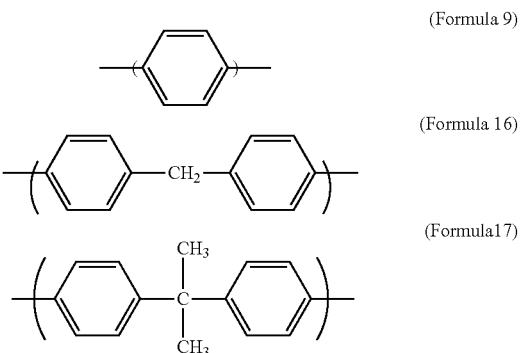

(Formula 9)

(Formula 16)

(Formula 17)

-continued

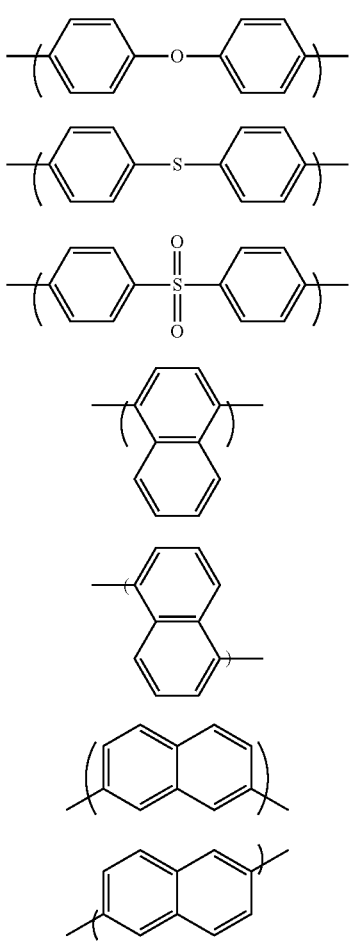

(Formula 18)

(Formula 19)

(Formula 20)

(Formula 21)

(Formula 22)

(Formula 23)

(Formula 24)

$R^2$ is cyclic aliphatic or organic aromatic;

an adhesive spacer, connected to the surfaces between the film layer and the second transparent conductive layer, and the film layer, the second transparent conductive layer, and the adhesive spacer form a cell; and an electrolyte layer filled in the cell and composed of a reducible organic compound, an electrolyte, and a solvent.

20. The electrochromic element as claimed in claim 19, wherein the electrolyte layer further comprises a second oxidizable organic compound of Formula 41, Formula 42, Formula 43, Formula 44, Formula 45, or a combination thereof:

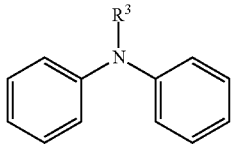

(Formula 41)

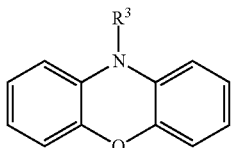

(Formula 42)

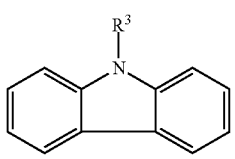

(Formula 43)

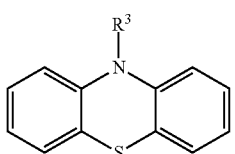

(Formula 44)

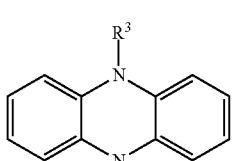

(Formula 45)

wherein $R^3$ is H or $C_1$~$C_{12}$ alkyl.

21. The electrochromic element as claimed in claim 19, wherein a distance between the first transparent conductive layer and the second transparent conductive layer is 10 μm~500 μm.

* * * * *